US008668912B2

(12) United States Patent
Kleven et al.

(10) Patent No.: US 8,668,912 B2
(45) Date of Patent: Mar. 11, 2014

(54) MYCOPLASMA GALLISEPTICUM FORMULATION

(75) Inventors: Stanley H. Kleven, Athens, GA (US); Naola M. Ferguson, Loganville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 13/140,929

(22) PCT Filed: Jan. 22, 2010

(86) PCT No.: PCT/US2010/021749
§ 371 (c)(1),
(2), (4) Date: Aug. 9, 2011

(87) PCT Pub. No.: WO2010/085611
PCT Pub. Date: Jul. 29, 2010

(65) Prior Publication Data
US 2012/0021005 A1    Jan. 26, 2012

Related U.S. Application Data

(60) Provisional application No. 61/146,472, filed on Jan. 22, 2009.

(51) Int. Cl.
 *A61K 39/02* (2006.01)
 *A61P 31/04* (2006.01)
 *C12N 1/20* (2006.01)

(52) U.S. Cl.
USPC .................................. 424/264.1; 435/252.1

(58) Field of Classification Search
None
See application file for complete search history.

(56) References Cited

U.S. PATENT DOCUMENTS

| | | | |
|---|---|---|---|
| 5,196,514 | A | 3/1993 | Avakian et al. |
| 5,846,527 | A | 12/1998 | Miller et al. |
| 7,217,420 | B2 | 5/2007 | Kleven et al. |
| 2006/0252110 | A1 | 11/2006 | Gregory et al. |
| 2006/0257414 | A1* | 11/2006 | Kleven et al. ............... 424/184.1 |
| 2007/0178115 | A1 | 8/2007 | Tang et al. |

FOREIGN PATENT DOCUMENTS

| WO | WO 2004/006851 A2 | 1/2004 |
|---|---|---|
| WO | WO 2004/006851 A3 | 3/2004 |

OTHER PUBLICATIONS

Colman (Res. Immunology, Jan. 1994, vol. 145, pp. 33-36; e.g. p. 33, col. 2).*
Greenspan et al. (Nature Biotechnology 7: 936-937, 1999).*
Boguslavsky et al., "Molecular characterization of the *Mycoplasma gallisepticum* pvpA gene which encodes a putative variable cytadhesin protein," Jul. 2000, *Infect Immun*; 68:3956-3964.
Charlton et al., "Complementary randomly amplified polymorphic DNA (RAPD) analysis patterns and primer sets to differentiate *Mycoplasma gallisepticum* strains," Mar. 1999, *J Vet Diagn Invest*; 11:158-161.
Charlton et al., "Randomly amplified polymorphic DNA (RAPD) analysis of *Mycoplasma gallisepticum* isolates from turkeys from the central valley of California," Sep. 1999, *J Vet Diagn Invest* 11, 408-415.
Fan et al., "Application of polymerase chain reaction with arbitrary primers to strain identification of *Mycoplasma gallisepticum*," Oct.-Dec. 1995, *Avian Dis*; 39:729-735.
Farmer et al., "Susceptibility of a naïve population of house finches to *Mycoplasma gallisepticum*," 2002, *J. Wildlife Dis*; 38:282-286.
"F Vax-MG®," datasheet. Schering-Plough Animal Health Corporation: Summit, NJ. Copyright dates © 1988, 1990, 1992. 2 pages.
Ferguson, Naola, "The Evaluation of a Live *Mycoplams gallisepticum* vaccine candidate and DNA sequence analysis in the molecular epidemiology of *Mycoplasma gallisepticum*," Doctoral Dissertation submitted to the University of Georgia (Athens, GA). Cover date 2003.
Ferguson et al., "Use of molecular diversity of *Mycoplasma gallisepticum* by gene-targeted sequencing (GTS) and random amplified polymorphic DNA (RAPD) analysis for epidemiological studies," Jun. 2005, *Microbiol*; 151:1883-1893.
Gaunson et al., "Lymphocytic infiltration in the chicken trachea in response to *Mycoplasma gallisepticum* infection," May 2000, *Microbiology*; 146:1223-1229.
Gautier-Bouchardon et al., "In vitro development of resistance to enrofloxacin, erythromycin, tylosin, tiamulin and oxytetracycline in *Mycoplasma gallisepticum, Mycoplasma iowae* and *Mycoplasma synoviae*," Aug. 2, 2002, *Vet Microbiol*; 88:47-58.
Goh et al., "Molecular and biochemical analysis of a 105 kDa *Mycoplasma gallisepticum* cytadhesin (GapA)," Nov. 1998, *Microbiol*; 144:2971-2978.
Hnatow et al., "Characterization of MGC2, a *Mycoplasma gallisepticum* cytadhesin with homology to the *Mycoplasma pneumoniae* 30-kilodalton protein P30 and *Mycoplasma genitalium* P32," Jul. 1998, *Infect Immun*; 66:3436-3442.
Keeler et al., "Cloning and characterization of a putative cytadhesin gene (mgc1) from *Mycoplasma gallisepticum*," May 1996, *Infect Immun*; 64:1541-1547.
Kempf, "DNA amplification methods for diagnosis and epidemiological investigations of avian mycoplasmosis," 1998, *Avian Pathol*; 27:7-14.
Khan et al., "*Mycoplasma gallisepticum* species and strain-specific recombinant DNA probes," Jan. 1989, *Avian Pathol*; 18:135-146.
Levisohn and Kleven, "Avian mycoplasmosis (*Mycoplasma gallisepticum*)," Aug. 2000, *Rev Sci Tech*; 19:425-442.
Ley et al., "Molecular epidemiologic investigations of *Mycoplasma gallisepticum* conjunctivitis in songbirds by random amplified polymorphic DNA analyses," Jul.-Sep. 1997, *Emerg Infect Dis*; 3:375-380.

(Continued)

*Primary Examiner* — Robert A Zeman
(74) *Attorney, Agent, or Firm* — Mueting, Raasch & Gebhardt, P.A.

(57) ABSTRACT

The present invention provides a formulation that prevents virulent *Mycoplasma* gallHsepticum infection in birds of the order GalHf ormes. The formulation comprises live *Mycoplasma* gallHsepticum strain K5831 or derivatives thereof in a pharmaceutically acceptable carrier. A vaccine that prevents virulent *Mycoplasma* gallHsepticum infection in birds of the order Galliformes is also presented. Methods for administering the formulation and vaccine are also presented.

23 Claims, 8 Drawing Sheets

(56) References Cited

OTHER PUBLICATIONS

Liu et al., "Molecular variability of the adhesin-encoding gene *pvpA* among *Mycoplasma gallisepticum* strains and its application in diagnosis," May 2001, *J Clin Microbial*; 39:1882-1888.

"*Mycoplasma gallisepticum* Vaccine (TS-11)," datasheet. Merial Select, Gainesville, GA. No Copyright Date Listed. Available online [retrieved on Aug. 24, 2012]. Retrieved from the Internet: <http://www.drugs.com/vet/mycoplasma-gallisepticum-vaccine-ts-11.html?printable=1>; 3 pages.

"Mycovac-L®," datasheet. Intervet, Inc.: Millsboro, DE. No Copyright Date Listed. Available online [retrieved on Aug. 24, 2012]. Retrieved from the Internet: <http://www.drugs.com/vet/mycovac-1.html?printable=1>; 5 pages.

Nagamoto et al., "Comparative studies of the persistence of animal mycoplasmas under different environmental conditions," 2001, *Vet Microbial*; 82:223-232.

National Center for Biotechnology Information, National Library of Medicine, National Institutes of Health, GenBank Locus AY556238, Accession No. AY556238, "*Mycoplasma gallisepticum* strain K2101CK84 Mgc2 (mgc2) gene, partial cds," [online]. Bethesda, MD [retrieved on Aug. 24, 2012]. Retrieved from the Internet: <http://www.ncbi.nlm.nih.gov/nuccore/AY556238>; 1 page.

"Poulvac® Aero," datasheet. Fort Dodge Animal Health: Fort Dodge, IA. Copyright © 2006. Available online [retrieved on Aug. 24, 2012]. Retrieved from the Internet: <http://www.drugs.com/vet/poulvac-aero.html?printable=1>; 3 pages.

Papazisi et al., "The complete genome sequence of the avian pathogen *Mycoplasma gallisepticum* strain R(low)," Sep. 2003, *Microbial*; 149:2307-2316.

Raviv et al., "The *Mycoplasma gallisepticum* 16S-23S rRNA intergenic spacer region sequence as a novel tool for epizootiological studies," 2007, *Avian Dis*; 51:555-560.

Raviv et al., "Strain differentiating real-time PCR for *Mycoplasma gallisepticum* live vaccine evaluation studies," May 25, 2008, *Veterinary Medicine*; 129(1-2):179-87. Available online on Nov. 22, 2007.

Rodwell and Whitcomb, "C14: Methods for Direct and Indirect Measurement of Mycoplasma Growth," in *Methods in Mycoplasmology*, vol. I. Razin and Tully (eds.). Academic Press: New York, NY; 1983. Cover page, publisher's pages, and pp. 185-197.

Yoshida et al., "Identification and Expression of a *Mycoplasma gallisepticum* surface antigen recognized by a monoclonal antibody capable of inhibiting both growth and metabolism," Jun. 2000, *Infect Immun*; 68:3186-3192.

Extended European Search Report and European Search Opinion. Issued on Sep. 19, 2012, by the European Patent Office. Patent Application No. 10733876.6. 9 total pages.

Thesis of Ziv Raviv. "The Role of *Mycoplasma synoviae* in Commercial Layer *E. coli* Peritonitis Syndrome and *Mycoplasma gallisepticum* Intraspecific Differential Methods". Submitted to the Graduate Faculty of the University of Georgia in Partial Fulfillment of the Requirements for the Degree—Doctor of Philosophy. Athens, Georgia. 2007. 169 total pages.

\* cited by examiner

| Lane | Kleven # | PDRC# | ID | RAPD Pattern |
|---|---|---|---|---|
| 1 | K2101 | | | |
| 2 | K5831 B-19 | | | K2101 |
| 3 | K5833-2 | 049949 | K5831B-19 + 5 | K2101 |
| 4 | R strain | | | |
| 5 | 6/85 | | | |
| 6 | ts-11 | | | |
| 7 | F | | | |
| 8 | negative | | | |
| 9 | 100 bp ladder | | | |

| Lane | Kleven # | PDRC# | ID | RAPD Pattern |
|---|---|---|---|---|
| 1 | K2101 | | | |
| 2 | K5887B-10 | 050397 | K5831B-19 challenged; trachea | K5831B-19 |
| 3 | K5887B-28 | 050397 | K5831B-19 challenged; air sac | K5831B-19 |
| 4 | K5887B-44 | 050397 | K5831B-19 challenged; lung | K5831B-19 |
| 5 | K5887B-50 | 050397 | K5831B-19 challenged; lung | K5831B-19 |
| 6 | K5887B-56 | 050397 | K5831B-19 challenged; lung | K5831B-19 |
| 7 | K5887B-62 | 050397 | K5831B-19 challenged; lung | K5831B-19 |
| 8 | K5887B-68 | 050397 | K5831B-19 challenged; lung | K5831B-19 |
| 9 | K5887C-20 | 050398 | K5833-2 challenged; trachea | K5831B-19 |
| 10 | K5887C-29 | 050398 | K5833-2 challenged; air sac | K5831B-19 |
| 11 | K5887D-13 | 050399 | R challenged; trachea | R |
| 12 | K5887D-25 | 050399 | R challenged; air sac | Did not amplify |
| 13 | R strain | | | |
| 14 | K5831 B-19 | | | |
| 15 | negative | | | |
| 16 | | | 100 bp ladder | |

SEQUENCE LISTING

```
<160> NUMBER OF SEQ ID NOS: 18

<210> SEQ ID NO 1
<211> LENGTH: 20
<212> TYPE: DNA
<213> ORGANISM: artificial
<220> FEATURE:
<223> OTHER INFORMATION: synthetic oligonucleotide primer

<400> SEQUENCE: 1
ctcaagaacc aactcaacca                                          20

<210> SEQ ID NO 2
<211> LENGTH: 22
<212> TYPE: DNA
<213> ORGANISM: artificial
<220> FEATURE:
<223> OTHER INFORMATION: synthetic oligonucleotide primer

<400> SEQUENCE: 2
ggattaggac caaattgcgg at                                       22

<210> SEQ ID NO 3
<211> LENGTH: 23
<212> TYPE: DNA
<213> ORGANISM: artificial
<220> FEATURE:
<223> OTHER INFORMATION: synthetic oligonucleotide primer

<400> SEQUENCE: 3
caaccaggat ttaatcaacc tcg                                      23

<210> SEQ ID NO 4
<211> LENGTH: 24
<212> TYPE: DNA
<213> ORGANISM: artificial
<220> FEATURE:
<223> OTHER INFORMATION: synthetic oligonucleotide primer

<400> SEQUENCE: 4
ttctagcgct ttagccctaa accc                                     24

<210> SEQ ID NO 5
<211> LENGTH: 24
<212> TYPE: DNA
<213> ORGANISM: artificial
<220> FEATURE:
<223> OTHER INFORMATION: synthetic oligonucleotide primer

<400> SEQUENCE: 5
cttgtggaac agcaacgtat tcgc                                     24
```

```
<210> SEQ ID NO 6
<211> LENGTH: 26
<212> TYPE: DNA
<213> ORGANISM: artificial
<220> FEATURE:
<223> OTHER INFORMATION: synthetic oligonucleotide primer

<400> SEQUENCE: 6
ccaggcattt aaaaatccca aagacc                                           26

<210> SEQ ID NO 7
<211> LENGTH: 25
<212> TYPE: DNA
<213> ORGANISM: artificial
<220> FEATURE:
<223> OTHER INFORMATION: synthetic oligonucleotide primer

<400> SEQUENCE: 7
ggatcccatc tcgaccacga gaaaa                                            25

<210> SEQ ID NO 8
<211> LENGTH: 21
<212> TYPE: DNA
<213> ORGANISM: artificial
<220> FEATURE:
<223> OTHER INFORMATION: synthetic oligonucleotide primer

<400> SEQUENCE: 8
gctttgtgtt ctcgggtgct a                                                21

<210> SEQ ID NO 9
<211> LENGTH: 20
<212> TYPE: DNA
<213> ORGANISM: artificial
<220> FEATURE:
<223> OTHER INFORMATION: synthetic oligonucleotide primer

<400> SEQUENCE: 9
cggtggaaaa ccagctcttg                                                  20

<210> SEQ ID NO 10
<211> LENGTH: 23
<212> TYPE: DNA
<213> ORGANISM: artificial
<220> FEATURE:
<223> OTHER INFORMATION: synthetic oligonucleotide primer

<400> SEQUENCE: 10
gccamtccaa ctcaacaagc tga                                              23

<210> SEQ ID NO 11
<211> LENGTH: 23
<212> TYPE: DNA
<213> ORGANISM: artificial
<220> FEATURE:
<223> OTHER INFORMATION: synthetic oligonucleotide primer

<400> SEQUENCE: 11
ggacgtsgtc ctggctggtt agc                                              23

<210> SEQ ID NO 12
<211> LENGTH: 495
<212> TYPE: DNA
<213> ORGANISM: Mycoplasma gallisepticum

<400> SEQUENCE: 12
atgagagctt ataaccaatt cattactaga gggttggaca gttatgtaaa tagtacaact

```
aaagggatta atattcccaa caacttatca tcagattctg gtggtaagtt gttaatgact    120
gcttctgata tgttcgatag ttttgacgta tcatttagtg cagcttatgt tcaacaatat    180
ttaaaacaaa ctaataatac taaccgtgat actgttggtg tagttcaatc agatattgat    240
gagatcaatc tgatgaataa tttcattaga gctaaggcaa atggtaacac aaccaacacc    300
tactcacaac agattactaa taattcatta ttaaaaactg gtgaagcgaa tcgaactact    360
gatccatatt acaatgctta tgcagattta gcagctggaa ctaaagatat ccacgaaatc    420
tttgaatgaa atgggatgaa gacagttgat tcttcgaaat cagataattc atcaacaaac    480
gtaatgagta aaaat                                                    495

<210> SEQ ID NO 13
<211> LENGTH: 456
<212> TYPE: DNA
<213> ORGANISM: Mycoplasma gallisepticum

<400> SEQUENCE: 13
ggtagtccta agttattagg tccaaaccaa gctggtcatc cacaacacgg accacgtccg     60
atgaatgctc atccaggtca accacgccct caacaagctg ccccacgtcc aatgggagct    120
ggtggatcta accaaccaag accaatgcca aatggtctac aaaacccaca aggtccacga    180
ccaatgaacc ctcaaggcga tcctcgtcct caaccagctg gtgtcagacc taacagccca    240
caaaattctc aaccacgccc aatgccaaat aaaccacaag gtccacgacc aatgggtgct    300
ccaaatcctc aaccaggccc tcaacaagct ggcccacgtc aatgggagt tggtggatct    360 aaccaaccaa gaccaatgcc aaatcgtcca caaaacccac aaggtccacg accaatgaac    420
cctcaaggcg atcctcgtcc tcaaccagct ggtgtc                              456

<210> SEQ ID NO 14
<211> LENGTH: 615
<212> TYPE: DNA
<213> ORGANISM: Mycoplasma gallisepticum

<400> SEQUENCE: 14
ttttatccag tagtgggtgc aggtgctggg ttgattgttg tttctttact cttgggttta     60
gggattggga ttccgatcgc taagaaaaaa gaaagaatga tgatccaaga acgtgaagaa    120
caccaaaaga tggttgaatc ccttggtata atcgaagaac aaaataaaac agaagcgatt    180
gagccaactg cagcagtgcc aactgaagaa gttaatactc aagaaccaac tcaaccagct    240
ggtgttaatg tagctaataa ccctcagatg gggatcaatc aaccaggatt taatcaacct    300
cagattaatc cgcaatttgg tcctaatccc caacaaagaa ttaacccaca gggctttggt    360
ggcccaatgc cacctaacca atgggaatg cgaccagggt ttaaccaaat gccccacaa    420 atgggaggaa tgccacctaa ccaaatggga atgcgaccag gtttaaccaa atgcccccca    480
caaatgggag gaatgccacc aagaccaaac ttccctaacc aaatgcctaa tatgaatcaa    540
ccaagaccag gtttcagacc acaacctggt ggtgggtgc cgatgggaaa taaagctgta    600
ggtgggttta atcac                                                    615

<210> SEQ ID NO 15
<211> LENGTH: 309
<212> TYPE: DNA
<213> ORGANISM: Mycoplasma gallisepticum

<400> SEQUENCE: 15
cctaaccgaa ttactaaccc attaatgaat agagataacg taatcggtca aggtgcgttc     60
```

```
attagtagaa atgatattcc atcatcattc tttgaaaaca aaattaatga tattgtaact      120
acagaagctg atggtaaaga agtattagat agtaaataca ttaattcaat ctatagatat      180
actccacctc aaaacaatcc tgatattaga ttaagattat tagtaattga tcgttctaga      240
gcaactaatg acttcattaa gttattacct caagtattag ttgatggcga atacgttgct      300
gttccacaa                                                              309

<210> SEQ ID NO 16
<211> LENGTH: 17
<212> TYPE: DNA
<213> ORGANISM: artificial
<220> FEATURE:
<223> OTHER INFORMATION: synthetic oligonucleotide primer

<400> SEQUENCE: 16
aggcagcagt agggaat                                                     17

<210> SEQ ID NO 17
<211> LENGTH: 13
<212> TYPE: DNA
<213> ORGANISM: artificial
<220> FEATURE:
<223> OTHER INFORMATION: synthetic oligonucleotide primer

<400> SEQUENCE: 17
gtaaaacgac ggc                                                         13

<210> SEQ ID NO 18
<211> LENGTH: 20
<212> TYPE: DNA
<213> ORGANISM: artificial
<220> FEATURE:
<223> OTHER INFORMATION: synthetic oligonucleotide primer

<400> SEQUENCE: 18
cataactaac ataagggcaa                                                  20
```

MYCOPLASMA GALLISEPTICUM FORMULATION

CONTINUING APPLICATION DATA

This application is the §371 U.S. National Stage of International Application No. PCT/US2010/021749, filed Jan. 22, 2010, which claims the benefit of U.S. Provisional Application Ser. No. 61/146,472, filed Jan. 22, 2009, which are incorporated by reference herein.

BACKGROUND

*Mycoplasma gallisepticum* (MG) is an infectious respiratory pathogen of chickens and turkeys. It is the most pathogenic and economically significant mycoplasma pathogen of poultry. Economic losses from condemnation or downgrading of carcasses, reduced feed and egg production efficiency, and increased medication costs are factors that make this one of the costliest disease problems confronting commercial poultry production worldwide. The control of MG is generally by isolation and maintenance of breeding stock free of MG. However, the rapid expansion of poultry production in small geographic areas and multiple-age farms that never depopulate make the eradication and control of MG by such biosecurity efforts alone difficult and necessitate the implementation of additional measures. In these situations, prophylactic immunization of fowl against MG related disease involves the use of inactivated vaccines or exposure to live attenuated vaccine strains of MG. See, for example, Kleven et al., 1997, *Acta Vet Hung;* 45(3):299-305.

However, each approach has disadvantages. Inactivated vaccines, while generally effective in protecting against loss of egg production in layers, do not reliably prevent infection or provide consistent protection against respiratory disease. And, while live attenuated MG vaccines appear to be more effective, and therefore more popular, than inactivated vaccines, they can produce disease or impair reproductive function.

An important characteristic of an effective MG live vaccine is the ability to increase resistance to wild-type strain infection, and to displace wild-type strains with the vaccine strain on multiple-age production sites (Levisohn and Kleven, 2000, *Rev Sci Tech;* 19(2):425-42; and Turner and Kleven, 1998, *Avian Dis;* 42(2):404-7). Currently, live vaccines available for the control of MG include F strain (Luginbuhl et al., 1967, *Ann NY Acad Sci;* 143:234-238; Adler et al., 1960, *Am J Vet Res;* 21:482-485), 6/85 (Evans and Hafez, 1992, *Avian Dis;* 36:197-201) and ts-11 (Whithear et al., 1990, *Aust Vet J;* 67:159-165; and Whithear et al., 1990, *Aust Vet J;* 67:168-174). F strain is transmissible to unvaccinated pen mates and chickens in adjacent pens and can be isolated from farms long after vaccination has ceased. The strains ts-11 and 6/85 are transmissible, albeit poorly, from vaccinated to unvaccinated poultry when in contact. F strain persists at higher levels in the upper respiratory tract than either ts-11 or 6/85, and ts-11 appears to colonize more effectively than 6/85. F-strain also transmits from hen to egg. Unfortunately, although each of the currently available vaccines has its advantages, none of them attains the ideal status in every respect. Thus, there is therefore a need for improved live MG vaccine strains that are both safe and efficacious, that are stable and non-virulent.

SUMMARY OF THE INVENTION

The present invention includes an isolated *Mycoplasma gallisepticum* strain, wherein the isolated *Mycoplasma gallisepticum* strain is the K5831 *Mycoplasma gallisepticum* strain deposited at the ATCC under Patent Designation PTA-9495.

The present invention includes an essentially biologically pure culture of the K5831 *Mycoplasma gallisepticum* strain deposited at the ATCC under Patent Designation PTA-9495.

The present invention includes an isolated *Mycoplasma gallisepticum* strain, wherein the isolated *Mycoplasma gallisepticum* strain is the K5831 *Mycoplasma gallisepticum* strain deposited at the ATCC under Patent Designation PTA-9495, or a progeny or derivative thereof, wherein a progeny or derivative thereof has the same biological, serological, and/or genetic characteristics of the K5831 *Mycoplasma gallisepticum* strain deposited at the ATCC under Patent Designation PTA-9495.

The present invention includes an essentially biologically pure culture of the K5831 *Mycoplasma gallisepticum* strain deposited at the ATCC under Patent Designation PTA-9495, or a progeny or derivative thereof, wherein a progeny or derivative thereof has essentially the same biological and serological characteristics of the K5831 *Mycoplasma gallisepticum* strain deposited at the ATCC under Patent Designation PTA-9495.

In some embodiments of the present invention, the isolated *Mycoplasma gallisepticum* strain, progeny or derivative thereof is lyophilized.

The present invention includes a composition including an isolated *Mycoplasma gallisepticum* strain, progeny or derivative thereof as described herein. In some embodiments, a composition may further include water. In some embodiments, a composition may further include a pharmaceutically acceptable carrier. In some embodiments, a composition may be formulated for mucosal administration. In some embodiments, a composition may be formulated for intranasal, intraocular, or oral administration. In some embodiments, a composition may be formulated for spraying or aerolizing.

The present invention includes a vaccine including an isolated *Mycoplasma gallisepticum* strain, progeny or derivative thereof, as described herein, or a composition as described herein. In some embodiments, a vaccine may reduce the susceptibility of a birds of the order Galliformes to disease induced by *Mycoplasma gallisepticum*.

The present invention includes a vaccine for birds of the order Galliformes including an amount of the K5831 *Mycoplasma gallisepticum* strain, deposited at the ATCC under Patent Deposit Designation PTA-9495 or a derivative thereof, sufficient to protect the birds from disease induced by *Mycoplasma gallisepticum*, and a pharmaceutically acceptable carrier. In some embodiments, a protective amount is that amount required for the K8531 *Mycoplasma gallisepticum* strain to colonize the upper respiratory tract of the bird. In some embodiments, a protective amount is between about 50 and about $5 \times 10^7$ ccu/bird.

The present invention includes a method for reducing susceptibility of a bird of the order Galliformes against disease induced by *Mycoplasma gallisepticum*, the method including administering to the bird the K5831 *Mycoplasma gallisepticum* strain deposited at the ATCC under Patent Deposit Designation PTA-9495, or a progeny or derivative thereof.

The present invention includes a method for reducing susceptibility of a bird of the order Galliformes against disease induced by *Mycoplasma gallisepticum*, the method including administering an isolated *Mycoplasma gallisepticum* strain, progeny or derivative as described herein, a composition as described herein, or a vaccine as described herein to the bird.

The present invention includes a method for protecting a bird of the order Galliformes against disease induced by

*Mycoplasma gallisepticum*, the method including administering to the bird the K5831 *Mycoplasma gallisepticum* strain deposited at the ATCC under Patent Deposit Designation PTA-9495, or a progeny or derivative thereof.

The present invention includes a method for protecting a bird of the order Galliformes against disease induced by *Mycoplasma gallisepticum*, the method including administering an isolated *Mycoplasma gallisepticum* strain, progeny or derivative as described herein, a composition as described herein, or a vaccine as described herein to the bird.

In some aspects of the methods of the present invention, the K5831 *Mycoplasma gallisepticum* strain or progeny or derivative thereof persists in the respiratory epithelium of the bird. In some aspects of the methods of the present invention, the K5831 *Mycoplasma gallisepticum* strain or progeny or derivative thereof excludes other *Mycoplasma gallisepticum* strains from the respiratory epithelium. In some aspects of the methods of the present invention, the K5831 *Mycoplasma gallisepticum* strain or progeny or derivative thereof is administered to the respiratory mucosa. In some aspects of the methods of the present invention, the K5831 *Mycoplasma gallisepticum* strain or progeny or derivative thereof is administered by eye drops. In some aspects of the methods of the present invention, the K5831 *Mycoplasma gallisepticum* strain or progeny or derivative thereof is administered nasally. In some aspects of the methods of the present invention, the K5831 *Mycoplasma gallisepticum* strain or progeny or derivative thereof is administered by aerosol. In some aspects of the methods of the present invention, the K5831 *Mycoplasma gallisepticum* strain or progeny or derivative thereof is administered by drinking water. In some aspects of the methods of the present invention, the method further includes administering at least one additional booster formulation to the bird. In some aspects of the methods of the present invention, the bird may be a chicken or turkey.

The terms "comprises" and variations thereof do not have a limiting meaning where these terms appear in the description and claims.

Unless otherwise specified, "a," "an," "the," and "at least one" are used interchangeably and mean one or more than one.

DETAILED DESCRIPTION OF ILLUSTRATIVE EMBODIMENTS OF THE INVENTION

Figure 1:
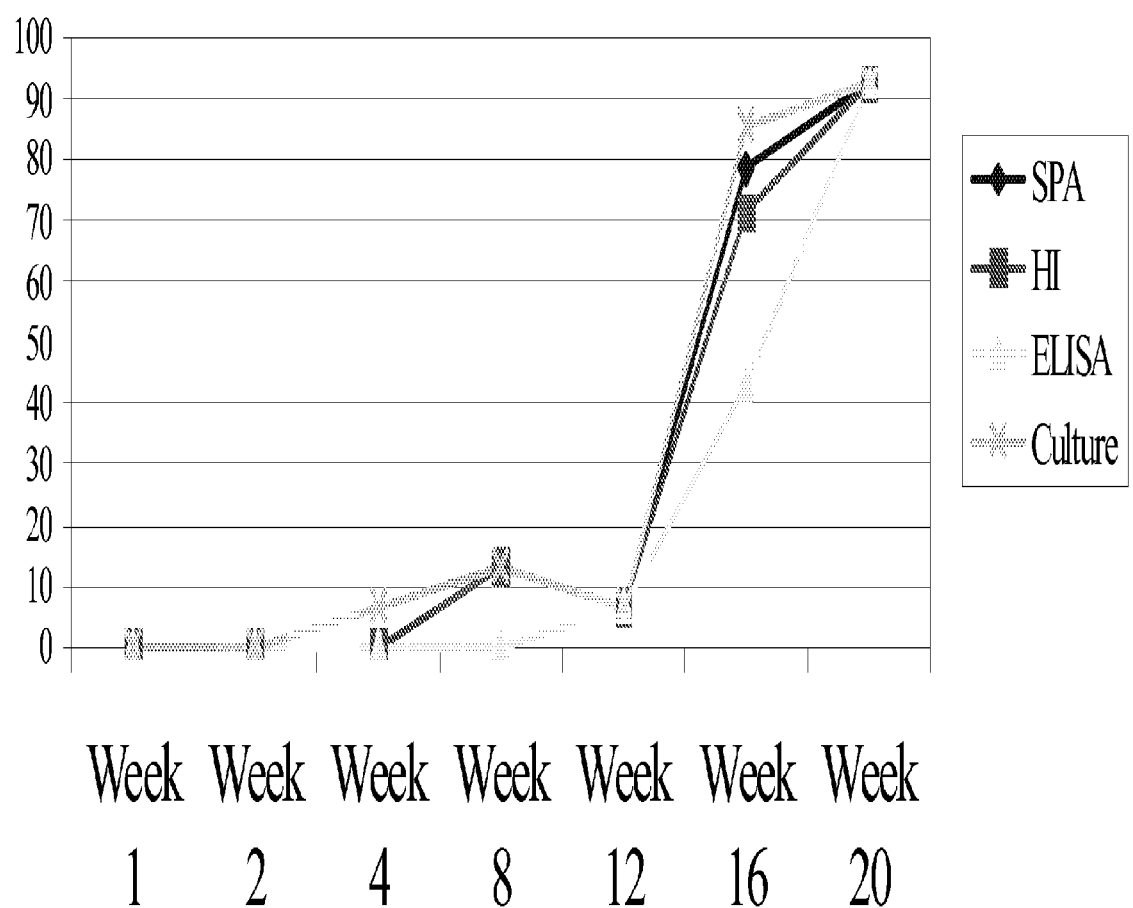
FIG. 1 is a graph depicting the summary of results for a direct-contact transmissibility study. Results are shown as % positive.

The present invention provides *Mycoplasma gallisepticum* (MG) strain K5831, progeny, and derivatives thereof that are avirulent, immunogenic, and stable when administered as live formulations. Formulations of the *Mycoplasma gallisepticum* of the present invention are safe and efficacious to inhibit *Mycoplasma gallisepticum* infections and will be useful in reducing the incidence and severity of disease of *Mycoplasma gallisepticum* infections in birds.

*Mycoplasma gallisepticum* strain K5831 was deposited with the American Type Culture Collection (ATCC®), 10801 University Boulevard, Manassas, Va. 20110-2209, USA, as PTA-9495 on Sep. 15, 2008. This strain was deposited in accordance with the Budapest Treaty on the International Recognition of the Deposit of Microorganisms for the Purposes of Patent Procedure. *Mycoplasma gallisepticum* strain K5831 is also referred to herein as *Mycoplasma gallisepticum* strain K5831B-19, MG K5831, MG K5831B-19, MG strain K5831, MG strain K5831B-19, K5831, K5831B-19, ATCC PTA-9495, and PTA-9495. *Mycoplasma gallisepticum* strain K5831 was isolated from chickens challenged with *Mycoplasma gallisepticum* strain K2101 (MG K2101). MG K2101 was a field isolate, isolated in Colorado in 1984 from a commercial layer flock demonstrating drops in egg protection. Of approximately thirty isolates, isolates B-1 to B-30, isolate MG K5831B-19 was selected for further characterization and analysis.

The present invention includes the isolated *Mycoplasma gallisepticum* (MG) strain K5831 that was deposited with the ATCC Patent Deposit Designation as PTA-9495, on Sep. 15, 2008. As used herein, "isolated" refers to material removed from its original environment (e.g., the natural environment if it is naturally occurring), and thus is altered "by the hand of man" from its natural state. Also included in the present invention are isolated progeny and isolated derivatives of *Mycoplasma gallisepticum* strain K5831 ATCC Patent Deposit Designation PTA-9495 and strains with equivalent or similar biological, serological, and/or genetic characteristics. As used herein, serological, biological, and genetic characteristics may include one or more of the characteristics described in the data in the Examples and Figures included herewith. More particularly, progeny or derivative strains of the PTA-9495 material retain the particularly favorable protective properties belonging to the present invention. Progeny of *Mycoplasma gallisepticum* strain K5831 ATCC Patent Deposit Designation PTA-9495 may be obtained by any of the various methods for propagating *Mycoplasma gallisepticum* known in the art, including, for example, in vitro culture or back passage in an bird. Examples of progeny include, for example, re-isolates K5866, K5969, K5872, and K5876, and K5883-2, as described in Example 3. Derivatives of *Mycoplasma gallisepticum* strain K5831 ATCC Patent Deposit Designation PTA-9495 shall include genetically modified versions of the deposited MG K5831 strain. Such manipulations include, but are not limited to, mutagenizing the MG strain or introducing genes or gene cassettes encoding alternative proteins or nonfunctional proteins, or noncoding nucleotide sequences into the MG organism.

MG strain K5831 and progeny and derivatives thereof may be identified and differentiated from other *M. gallisepticum* strains using any of the many techniques that have been developed for the differentiation of *M. gallisepticum* strains, including, for example, protein profile analysis (Khan et al., 1987, *Avian Dis;* 31:315-320), restriction fragment length polymorphism (RFLP) (Kleven et al., 1988, *Avian Dis;* 32:731-741), ribotyping (Yogev et al., 1988, *Avian Dis;* 32:220-231), strain-specific DNA probes (Khan et al., 1989, *Avian Pathol;* 18:135-146), PCR with strain-specific primers (Nascimento et al., 1993, *Avian Dis;* 37:203-211), and random amplified polymorphic DNA (RAPD) (Charlton et al., 1999, *J Vet Diag Invest;* 11:158-161; Fan et al., 1995, *Avian Dis* 39; 729-735; and Geary et al., 1994, *Mol Cell Probes;* 8:311-316). The RAPD method has been successfully utilized to identify vaccine strains in both experimental and field conditions (Ley et al., 1997, *Avian Dis;* 41:187-194; Kleven and Fan, 1998, *Avian Dis;* 42:300-306; Turner and Kleven 1998, *Avian Dis* 42; 404-407), as well as for tracking epidemiologically related isolates in the field (Kempf, 1998, *Avian Pathol;* 27:7-14; Ley et al., 1997, *Emerg Infect Dis;* 3:375-380; Charlton et al., 1999, *J Vet Diagn Invest* 11, 408-415; Levisohn & Kleven, 2000, *Rev Sci Tech;* 19:425-442). Progeny or derivatives of K5831 may share one or more of the identifying characteristics of MG strain K5831. Progeny or derivatives of K5831 may share substantially all such identifying characteristics. The present invention also contemplates, in further aspects, the parental MG K2101 strain, progeny and derivatives thereof and their use in any of the compositions, vaccine, and methods described herein.

Figure 7:
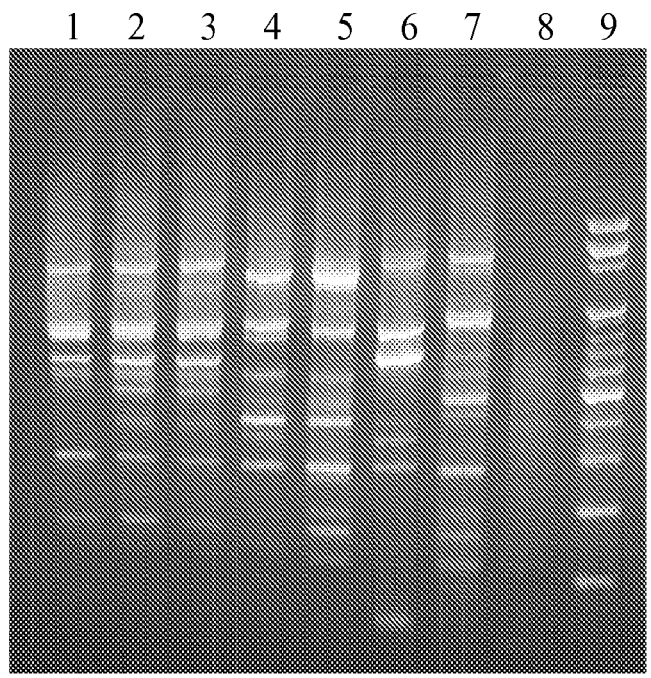
FIG. 7 presents the results of Random Amplified Polymorphic DNA (RAPD) analysis to fingerprint K5831B-19 and back passage isolate K5883-2. Lane 1 is K2101. Lane 2 is K5831B-19. Lane 3 is K5833-2. Lane 4 is R strain. Lane 5 is 6/85. Lane 6 is ts-11. Lane 7 is F strain. Lane 8 is a negative control. Lane 9 is the 100 bp ladder.
Figure 8:
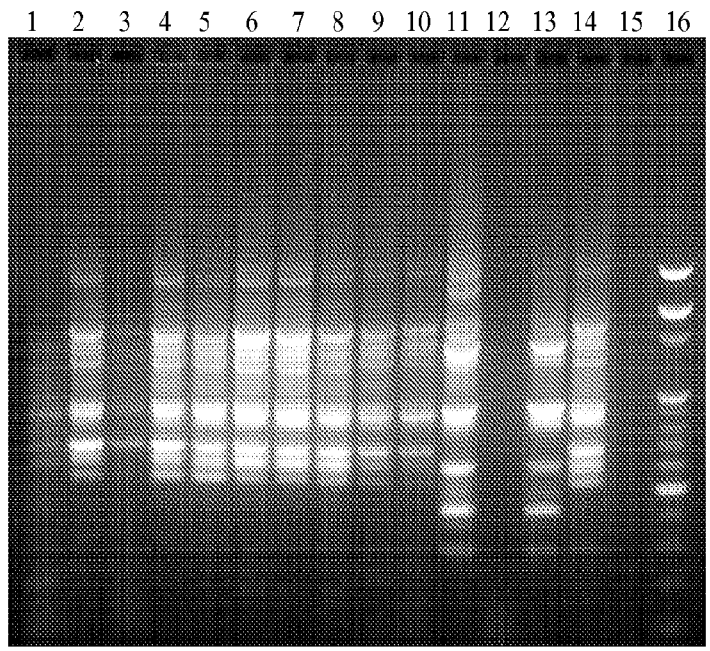
FIG. 8 presents results of Random Amplified Polymorphic DNA (RAPD) analysis to fingerprint K5831B-19 back passage isolates ten days post challenge with K5831B-19, K882-1, or R strain.

MG strain K5831, progeny and derivatives thereof may be identified and differentiated from other *M. gallisepticum* strains using Random Amplified Polymorphic DNA (RAPD) analysis using. Briefly, arbitrary primed polymerase chain reactions (AP-PCR) involving three cycles of low stringency amplification followed by PCR at higher stringency is performed with three arbitrarily chosen primers, using procedures described in more detail by Fan et al. (Fan et al., 1995, *Avian Dis;* 39:729-735). The three oligonucleotide primers used are M16SPCR5' (AGGCAGCAGTAGGGAAT (SEQ ID NO:16)); M13F (GTAAAACGACGGC (SEQ ID NO:17)); and S1OLIGO3' (CATAACTAACATAAGGGCAA (SEQ ID NO:18)). Representative results of such RAPD analysis for K5831B-19 and progeny K5833-2 are shown in FIGS. 7 and 8. Progeny and derivatives thereof may demonstrate a substantially equivalent RAPD profile of *Mycoplasma gallisepticum* strain K5831 ATCC Patent Deposit Designation as PTA-9495 when the Fan primers are utilized.

K5831, progeny or derivative thereof may be identified and differentiated from other *M. gallisepticum* strains using a gene-targeted sequencing (GTS) approach. Any of a variety of genes may be analyzed. For example, genetic sequences of the gapA gene, the mgc2 gene, the pvpA gene and/or the gene encoding a predicted conserved surface lipoprotein may be used. These four gene sequences were first identified in the genome of *M. gallisepticum* $R_{low}$ strain (Papazisi et al., 2003, *Microbiol;* 149:2307-2316). The gapA gene encodes a protein shown to be involved in the cytadhesion process (Goh et al., 1998, *Microbiol;* 144:2971-2978) identified as genome coding DNA sequence (CDS) MGA_0934. The mgc2 gene encodes a second cytadhesin protein also known to play a role in the attachment process (Hnatow et al., 1998, *Infect Immun;* 66:3436-3442) identified as genome CDS MGA_0932. The pvpA gene encodes a putative accessory cytadhesin that exhibits size variation among *M. gallisepticum* strains (Boguslaysky et al., 2000, *Infect Immun;* 68:3956-3964; Liu et al., 2001, *J Clin Microbiol;* 39:1882-1888). The gene encoding a predicted conserved surface lipoprotein, originally recognized by Nascimento et al. (Nascimento et al. 1991, *Avian Dis;* 35:62-69), was identified as genome CDS MGA_0319 (Papazisi et al., 2003, Microbiology; 149:2307-2316).

Progeny or derivatives of K5831 may share one or more of the identifying sequences of *Mycoplasma gallisepticum* strain K5831B in portions of the cytadhesin pvpA gene (SEQ ID NO:13), the cytadhesin gapA gene (SEQ ID NO:15), the cytadhesin mgc2 gene (SEQ ID NO:14), or the uncharacterized hypothetical surface lipoprotein-encoding gene designated genome coding DNA sequence (CDS) MGA_0319 (SEQ ID NO:12), as determined by the gene-targeted sequencing (GTS) analysis described in more detail in Example 8, following, for example, procedures described in more detail in Ferguson et al. (Ferguson et al., 2005, *Microbiol;* 151:1883-1893).

MG strain K5831 and progeny or derivatives thereof may demonstrate a Taqman real-time PCT standard curve with one or more of a mean $C_T$ value of 37.20, 33.48, 30.48, 27.15, 23.97, 20.74, 17.28, and 13.70 for template $\log_{10}$ copy number of 1, 2, 3, 4, 5, 6, 7, and 8, respectively; a linear equation of y=−0.3021x+12.203; and/or a R-squared value if 0.9996. Such a Taqman real-time PCT may utilize primers from the mgc2 gene, GenBank Accession Number AY556238, such as, for example, using a forward primer sequence (5'→3') including nucleotides 218 to 237 of AY556238 (CTCAAGAAC-CAACTCAACCA (SEQ ID NO:1)), a reverse primer sequence (5'-3') including nucleotides 329 to 308 of AY556238 (GGATTAGGACCAAATTGCGGAT (SEQ ID NO:2)), a dual labeled probe sequence (5'→3') including nucleotides 280 to 303 of AY556238 (CAACCAGGATT-TAATCAACCTCG (SEQ ID NO:3)), and an anneling/extension temperature of 61° C. Alternatively, similar probes from the mgc2 gene, GenBank Accession No AY556282, may be used. The methodology for such a determination is described in more detail by Raviv et al. (Raviv et al., 2008, Veterinary Medicine; 129(1-2):179-87). Progeny or derivatives of K5831 may share one or more of the identifying characteristics of MG strain K5831 determined by such a Taqman real-time PCR assay.

*Mycoplasma gallisepticum* strains of the present invention demonstrate a variety of additional biological and/or serological characteristics, including, but not limited to any of those described in the examples included herewith. For example, *Mycoplasma gallisepticum* strains of the present invention may demonstrate lowered rates of transmission. *Mycoplasma gallisepticum* strains of the present invention may demonstrate enhanced persistence in the upper respiratory tract. *Mycoplasma gallisepticum* strains of the present invention may demonstrate little or no increase in virulence when back passaged. *Mycoplasma gallisepticum* strains of the present invention may demonstrate limited or no vertical transmission. Vaccination with a *Mycoplasma gallisepticum* strain of the present invention may result in lower colonization with other *Mycoplasma gallisepticum* strains, such as for example, the R strain. Vaccination with a *Mycoplasma gallisepticum* strain of the present invention may result in gross lesions following challenge that remain primarily in the respiratory system of challenged birds.

With the present invention, *Mycoplasma gallisepticum* strain K5831 was evaluated by studies to investigate the minimum dose, transmissibility, persistence and excretion, back passage, body distribution, vertical transmission, displacement of virulent strains, pathogenicity in embroyonated eggs and chickens, and characterization of biochemical, biological and serological properties. The minimum titer of MG K5831 necessary to infect and induce adequate vaccine protection was about $6.22 \times 10^5$ CCU/ml. MG K5831 had a relatively low rate of transmission and persisted in the upper respiratory tract for at least five months. There was no increase in virulence of MG K5831 when back passaged five times through chickens and gross lesions following challenge were assessed. MG K5831 remained primarily in the respiratory system of challenged birds. No vertical transmission of MG K5831 was detected. And, vaccination with MG K5831 resulted in lower colonization with R strain The present invention includes compositions of the *Mycoplasma gallisepticum* strains, progeny and derivatives thereof described herein. Such compositions may serve as vaccines that reduce the susceptibility of a birds to disease induced by *Mycoplasma gallisepticum*. Such compositions may serve as vaccines that protect the birds from disease induced by *Mycoplasma gallisepticum*. Compositions and vaccines of the present invention may include, for example, water or culture medium. Such compositions and vaccines may include pharmaceutically acceptable carriers or diluents. Carriers include, for example, stabilizers, preservatives and buffers. Suitable stabilizers include, for example, SPGA, carbohydrates (such as sorbitol, mannitol, starch, sucrose, dextran, glutamate or glucose), proteins (such as dried milk serum, albumin or casein) or degradation products thereof. Suitable buffers include, for example, alkali metal phosphates. Suitable preservatives include, for example, thimerosal, merthiolate and gentamicin. Diluents, include, but are not limited to, water, aqueous buffer (such as buffered saline), alcohols, and polyols (such as glycerol).

MG strains, compositions and vaccines of the present invention may be substantially pure. As used herein, "substantially pure" will mean material essentially free of any similar macromolecules or other biological entities that would normally be found with it in nature.

Preferably the organisms used in such formulations are live. In some embodiments, the organisms, compositions, or vaccines may be lyophilized.

Compositions and vaccines of the present invention may be administered to birds of any of a variety of avian species that are susceptible to *Mycoplasma gallisepticum*, including, but not limited to, poultry, birds of the order Galliformes, and exotic bird species. Birds of the order Galliformes include, but are not limited to, chickens, turkeys, grouse, quails, and pheasants. As used herein, poultry includes domesticated birds that are kept for the purpose of collecting their eggs, or killing for their meat and/or feathers. These most typically are members of the superorder Galloanserae (fowl), especially the order Galliformes (which includes, for example, chickens, quail, turkeys, and grouse) and the family Anatidae (in order Anseriformes), commonly known as "waterfowl" (including, for example, ducks, geese, and swans). Poultry may also include other birds which are killed for their meat, such as pigeons or doves or birds considered to be game, like pheasants. Chickens include, but are not limited to, hens, roosters, broilers, roasters, layers, breeders, the offspring of breeder hens, and layers. As used herein, the term "susceptible to" means the possibility or actuality of a detrimental response to the referenced microorganism, such as, for example, reduced vigor or a failure to thrive, when compared to a non-susceptible individuals or groups, and/or one or more pathological state(s) indicative of *Mycoplasma gallisepticum* infection.

Compositions and vaccines of the present invention may be formulated for delivery by any of a variety of routes known in the veterinary arts, such as for example, mucosal, intranasal, intraocular, or oral administration. Compositions and vaccines of the present invention may be formulated for delivery to the respiratory mucosa and may be administered such that it is immediately or eventually brought into contact with the bird's respiratory mucosal membranes. Compositions and vaccines of the present invention may be formulated for delivery by any of a variety of modes known in the veterinary arts, such as for example, spraying or aerolizing. An immunogenic composition or vaccine of the present invention may be administered by any suitable known method of inoculating birds including, but not limited to, nasally, ophthalmically, by injection, in drinking water, in the feed, by exposure, in ovo, maternally, and the like.

The immunogenic composition or vaccine may be administered by mass administration techniques such as by placing the vaccine in drinking water or by spraying the animals' environment. A composition may be administered by spraying an individual or the flock with a solution, such aerosol delivery may involve the administration of the composition incorporated in small liquid particles. Such spray-type particles may have a droplet size ranging from between about 10 to about 100 microns, more preferably, a droplet size from between about <1 to about 50 microns. For the generation of the small particles, conventional spray-apparatus and aerosol generators may be used, such as the commercially available spray generators for knapsack spray, hatchery spray and atomist spray. Administration through drinking water may can be carried out using conventional apparatus. When administered by injection, the immunogenic composition or vaccine may be administered parenterally. Parenteral administration includes, for example, administration by intravenous, subcutaneous, intramuscular, or intraperitoneal injection.

A composition or vaccine of the present invention may be administered to birds before or after hatching. Birds may receive such a composition of vaccine at any of a variety of ages. With delivery after hatching, materials may be delivered, for example, about one week after hatching, about two weeks after hatching, about three weeks after hatching, about four weeks after hatching, about five weeks after hatching, about six weeks after hatching, or any range thereof. For in ovo administration, materials may be delivered about seventeen days of incubation, about eighteen days of incubation, about nineteen days of incubation, about twenty days of incubation, and any range thereof.

Compositions and vaccines of the present invention may adjusted to include a designated concentration of *Mycoplasma gallisepticum*. Organisms may be measured as color changing units. Color changing units, also referred to herein as "ccu," of *Mycoplasma gallisepticum* can be quantified using established standard methodology, including, for example, protocols set forth in Rodwell and Whitcomb (In "Methods in Mycoplasmology," Eds. Razin and Tully, 1993). For example, an effective amount may be administered to a single bird at one drop per eye per bird, one drop being approximately 0.05 ml, therefore with a concentration of between about $1 \times 10^3$ and about $1 \times 10^6$ color-changing units/ml (ccu/ml), this is equivalent to about 50 to about 50,000 ccu/bird. For example, a concentration; of about 50, about $1 \times 10^2$ ccu/ml, about $5 \times 10^2$ ccu/ml, about $1 \times 10^3$ ccu/ml, about $5 \times 10^3$ ccu/ml, about $1 \times 10^4$ ccu/ml, about $5 \times 10^4$ ccu/ml, about $1 \times 10^5$ ccu/ml, about $5 \times 10^5$ ccu/ml, about $1 \times 10^6$ ccu/ml, about $5 \times 10^6$ ccu/ml, about $1 \times 10^7$ ccu/ml, about $5 \times 10^7$ ccu/ml, and any range thereof (such as, for example, about $1 \times 10^5$ ccu/ml to about $1 \times 10^6$ ccu/ml), may be used.

*Mycoplasma gallisepticum* strains of the present invention may be administered to birds to reduce susceptibility to *Mycoplasma gallisepticum* infection. With such administration, the materials do not result in significant clinical signs or lesions indicative of *Mycoplasma gallisepticum*. The present materials persist, are not produced by genetic engineering, have low virulence, increased stability over many in vivo passages, have no increase in virulence when back passaged five times, and/or remain primarily in the respiratory system. The present materials do not transmit to eggs, or transmit to eggs a very low rate. Moreover, the present invention may displace virulent wild type strains and displace circulating endemic strains from poultry operations.

Accordingly, it is an object of the present invention to provide immunological materials that do not result in significant clinical signs or lesions indicative of MG disease. It is another object to provide immunological materials that persist in the upper respiratory tract for at least five months. It is another object to provide immunological materials that are not produced by genetic engineering. It is another object to provide immunological materials of low virulence. It is another object to provide immunological materials that have increased stability over many in vivo passages. It is another object to provide immunological materials with no increase in virulence when back passaged at least five times. It is another object to provide immunological materials that remain primarily in the respiratory system. It is another object to provide immunological materials that do not transmit to eggs, or transmit to eggs a very low rate. It is another object to provide immunological materials that prevent infection with virulent wild type strains and so displace circulating endemic strains from poultry operations.

Without wishing to be bound by any one particular theory, the MG strains of the present invention stimulate immunity and persist in the respiratory mucosa of treated birds, especially in the upper respiratory tract. Thus, a beneficial result of treatment of birds with the present materials is the ability of the materials to exclude virulent field strains from colonizing the upper respiratory tract. As used herein, "field" strains include any strains present in the environment of the birds, including wild type strains, or strains that are present in commingled poultry by virtue of previous attempts at vaccination. The amount administered may be that amount necessary to colonize the upper respiratory tract of any individual bird, or any given flock, preferably for a sufficient period to provide protection against invasion by virulent wild-type strains. The amount administered may be sufficient to colonize a bird's respiratory tract.

*Mycoplasma gallisepticum* (MG) strains of the present invention may be grown in culture according to, but not limited to, the following protocol. Frey's medium for the isolation of avian mycoplasmas:

Mycoplasma broth base 22.5 g
Dextrose 3 g
Swine serum 120 ml
Yeast Extract 35 ml
Phenol red (1%) 2.5 ml
Thallium acetate (10%)[A] 6 ml
Ampicillin 1 g/liter[A]
Combine reagents and q.s. to 1000 ml with distilled water.
[A]-Thallium acetate and ampicillin can be omitted when working with pure MG cultures, such as in commercial vaccine production.

Adjust pH to 7.8 with 20% NaOH and filter sterilize.

Other growth factors and preservatives can be used instead of the ones listed above without departing from the scope of the invention.

For agar medium use 1% of a purified agar such as ion agar #2, Noble agar, or Difco purified agar. All components except serum and ampicillin are sterilized by autoclaving at 121° C. for 15 minutes. Cool to 50° C. and aseptically add serum and ampicillin, which have been pre-sterilized by filtration and warmed to 50° C. Mix and pour plates to a depth of approximately 5 mm.

The invention also provides a kit including *Mycoplasma gallisepticum* strain K5831, and/or a progeny or derivative thereof described herein. The kit may include one or more containers filled with a *Mycoplasma gallisepticum* of the present invention. The *Mycoplasma gallisepticum* strain K5831 may be lyophilized. The kit may include additional, separate containers of other strains of *Mycoplasma gallisepticum* or other pathogens of poultry. Additionally, the kit may include other reagents such as buffers and solutions needed to practice the invention are also included. Optionally associated with such container(s) can be a notice or printed instructions. A kit of the present invention may include "packaging material." As used herein, the term "packaging material" refers to one or more physical structures used to house the contents of the kit. Packaging material is constructed by well known methods, preferably to provide a sterile, contaminant-free environment. Packaging material may be a solid matrix or a material such as glass, plastic, paper, foil, and the like. Thus, for example, a package can be a glass or plastic vial used to contain ccu quantities of *Mycoplasma gallisepticum* strain K5831.

The present invention is illustrated by the following examples. It is to be understood that the particular examples, materials, amounts, and procedures are to be interpreted broadly in accordance with the scope and spirit of the invention as set forth herein. For any method disclosed herein that includes discrete steps, the steps may be conducted in any feasible order. And, as appropriate, any combination of two or more steps may be conducted simultaneously.

EXAMPLES

Example 1

*Mycoplasma gallisepticum* Strain K5831 Minimum Dose Studies

This example investigates the minimum infectious dose and the minimum protective dose of *Mycoplasma gallisepticum* (MG) strain K5831 as a live vaccine in chickens. Eighty commercial layer type chickens were acquired at eight weeks of age from a source known to be free of MG and MS and housed in eight pens. The chickens were screened for the presence of mycoplasma by culture and serology upon arrival. The results of the pre-vaccination screen of the chickens were negative for the presence of mycoplasma and antibodies.

For serology screening, sera were analyzed for MG antibodies using the serum plate agglutination (SPA) test using commercial antigen (Intervet America, Millsboro, Del.), and the hemagglutination-inhibition (HI) test with antigen prepared from A5969 strain and chicken erythrocytes. The SPA and HI test were carried out according to procedures described by Kleven (Kleven, S. H. Mycoplasmosis. In: A Laboratory Manual for the Isolation and Identification of Avian Pathogens, Fourth Edition, Four ed. D. E. Swayne, J. R. Glisson, M. W. Jackwood, J. E. Pearson and W. M. Reed, eds. American Association of Avian Pathologists, Kennett Square, Pa. pp 74-80. 1998). An SPA score≥1 was considered positive. An HI titer of 1:20 was considered suspect and ≥1:40 was considered positive. Commercial enzyme-linked immunosorbent assays (ELISA) were also performed on the sera (IDEXX, Westbrook, Me.).

For the isolation and identification of mycoplasma, cotton swabs from choanal cleft, trachea, air sacs or various sites for body distribution were used for culture. The swabs were inoculated in Frey's modified broth and agar and incubated at 37° C. for a minimum of three weeks. *Mycoplasma* isolates were identified using direct immunofluorescence.

To determine the minimum infectious dose, six groups of twelve chickens were vaccinated via aerosol with dilutions of K5831B-19 from 10' color-changing units/ml (ccu/ml) to $10^2$ ccu/ml. At three days post challenge the chickens were swabbed and cultured for MG. At five weeks post vaccination the chickens were bled and cultured. A dose of $6.22 \times 10^6$ ccu/ml infected ten of the twelve chickens (83%); $6.22 \times 10^5$ ccu/ml infected four of twelve chickens (33%) and $6.22 \times 10^4$ ccu/ml infected two of twelve chickens (17%). At 33 days post vaccination the groups vaccinated with $6.22 \times 10^6$ ccu/ml and $6.22 \times 10^5$ ccu/ml of K5831B-19 were 100% positive for MG by culture. These findings are summarized in Table 1.

TABLE 1

Minimum Infectious Dose. MG isolation from the tracheas of chickens 3 days post vaccination (aerosol) with K5831B-19$^A$.

| Vaccine Dose | MG isolation (Trachea) |
|---|---|
| None | 0/11$^a$ |
| $6.22 \times 10^1$ | 0/11$^a$ |
| $6.22 \times 10^2$ | 0/7$^a$ |
| $6.22 \times 10^3$ | 0/9$^a$ |
| $6.22 \times 10^4$ | 2/12$^{ab}$ |
| $6.22 \times 10^5$ | 4/12$^b$ |
| $6.22 \times 10^6$ | 10/12$^c$ |

$^A$Values within a column with a different lower case superscript are significantly different (P ≤ 0.05)
$^B$No. of positive samples/No. of tested samples To determine the minimum protective dose, at six weeks post vaccination the chickens were challenged with R strain. One group served as non-vaccinated challenged controls and a second non-challenged group as negative controls. The birds were necropsied at ten days post challenge and evaluated by air sac lesion scoring, serology, culture and tracheal mucosa thickness and scoring. The groups vaccinated with $6.22 \times 10^6$ ccu/ml and $6.22 \times 10^5$ ccu/ml of K5831B-19 had significantly lower mean air sac lesion scores and mean tracheal mucosa measurements when compared to the non-vaccinated challenge controls. The vaccine dose of $6.22 \times 10^6$ ccu/ml also resulted in significantly fewer MG isolations from the air sacs of the birds when compared to the controls.

RAPD analysis of some of the isolates from the groups vaccinated with $6.22 \times 10^6$ ccu/ml and $6.22 \times 10^5$ ccu/ml of K5831B-19 showed that the isolates may be mixed cultures of R strain and K5831B-19. These results are summarized in Table 2.

Therefore, $6.22 \times 10^5$ ccu/ml of K5831B-19 is the minimum titer necessary to infect and induce adequate vaccine protection. Although only 33% of the chickens were initially infected by this dose, 30 days later 100% of the group were infected and protection was good. A titer of $6.22 \times 10^6$ ccu/ml resulted in better protection. This minimum dose may be affected by many factors including the method of administration, housing and environment.

Example 2

*Mycoplasma gallisepticum* Strain K5831
Transmissibility and Excretion

This example investigates the potential of *Mycoplasma gallisepticum* (MG) strain K5831 to transmit from infected chickens to naive chickens. The persistence (excretion) of K5831B-19 in the respiratory tract of vaccinated birds was investigated.

Procedure

One hundred and twenty-five male layer-type chickens were acquired from a source free of *Mycoplasma*. The birds were housed in pens. There were four groups (35, 15, 20 and 20 chickens in each pen) for the transmissibility study and one group of 35 chickens for the excretion study. At three weeks of age five chickens were screened for *Mycoplasma* by culture and serology.

Transmissibility. At four weeks of age 35 chickens in the seeder group of chickens were infected with K5831B-19 via aerosol. Five of these chickens were then commingled with the group of 15 direct contacts. Twenty chickens were placed in a pen immediately adjacent to the direct contacts (across-wire contacts). Another group of 20 chickens were placed in a pen separated from the direct contacts by an empty pen (across-empty-pen contacts). The fifteen direct contacts and five chickens from each of the across-wire contact and across-empty-pen contact groups were bled for serology and swabs were obtained for mycoplasma culture at 1, 2, 4, 8, 12, 16 and 20 weeks post inoculation of the seeders. The five old seeders were removed (bled and swabbed) and replaced with five new seeders at each bleeding/swabbing. At 20 weeks post inoculation all of the birds were bled, cultured and euthanized.

Excretion. At four weeks of age 35 chickens were inoculated with K5831B-19 via aerosol. At 1, 2, 4, 8, 12, 16 and 20 weeks post inoculation five chickens were removed and evaluated by serology, culture of tracheal and air sac swabs and histopathology of the trachea.

TABLE 2

Minimum Protective Dose. Serological response, lesion scores and MG isolation from chickens 10 days post challenge with R strain$^A$.

| Vaccine Dose | Challenge | SPA | HI | ELISA | Air sac lesion score | Tracheal mucosal thickness | MG isolation Choanal cleft | MG isolation Air sacs |
|---|---|---|---|---|---|---|---|---|
| None | No | 0/10$^B$ (0.0)$^{Ca}$ | 7/9 (1.2)$^{Da}$ | 0/10 (0.0)$^{Ea}$ | 0/10 (0.0)$^{Fa}$ | 70.7 ± 20.5$^{Ga}$ | 0/10$^a$ | 0/10$^a$ |
| None | Yes | 10/10 (2.9)$^{bc}$ | 8/8 (2.2)$^b$ | 10/10 (1.0)$^{ab}$ | 10/10 (3.1)$^b$ | 173.8 ± 60.6$^c$ | 10/10$^b$ | 10/10$^c$ |
| $6.22 \times 10^1$ | Yes | 10/10 (3.4)$^c$ | 9/9 (2.3)$^b$ | 10/10 (1.4)$^{bc}$ | 10/10 (3.1)$^b$ | 252.6 ± 59.8$^d$ | 10/10$^b$ | 10/10$^c$ |
| $6.22 \times 10^2$ | Yes | 9/10 (2.7)$^{bc}$ | 10/10 (2.4)$^b$ | 10/10 (2.0)$^{bcd}$ | 10/10 (3.1)$^b$ | 151.7 ± 59.2$^{bc}$ | 10/10$^b$ | 10/10$^c$ |
| $6.22 \times 10^3$ | Yes | 10/10 (3.3)$^c$ | 8/8 (2.3)$^b$ | 10/10 (1.6)$^{bc}$ | 9/10 (2.4)$^b$ | 175.9 ± 64.4$^c$ | 10/10$^b$ | 10/10$^c$ |

TABLE 2-continued

Minimum Protective Dose. Serological response, lesion scores and
MG isolation from chickens 10 days post challenge with R strain[A].

| Vaccine Dose | Challenge | SPA | HI | ELISA | Air sac lesion score | Tracheal mucosal thickness | MG isolation Choanal cleft | Air sacs |
|---|---|---|---|---|---|---|---|---|
| $6.22 \times 10^4$ | Yes | 10/10 (2.8)[bc] | 8/8 (2.3)[b] | 10/10 (2.5)[cd] | 10/10 (2.3)[b] | 186.7 ± 70.6[cd] | 10/10[b] | 10/10[c] |
| $6.22 \times 10^5$ | Yes | 10/10 (3.1)[bc] | 10/10 (2.3)[b] | 10/10 (3.1)[d] | 5/10 (1.1)[a] | 86.3 ± 13.8[ab] | 10/10[b] | 8/10[bc] |
| $6.22 \times 10^6$ | Yes | 10/10 (2.3)[b] | 9/9 (2.2)[b] | 10/10 (2.7)[d] | 1/10 (0.2)[a] | 96.1 ± 19.8[ab] | 10/10[b] | 7/10[b] |

[A]Values within a column with a different lower case superscript are significantly different (P ≤ 0.05)
[B]No. of positive samples/No. of tested samples (SPA: ≥1, HI: ≥20, ELISA: ≥0.5, Air sac score ≥1)
[C]Mean agglutination grade (from 0 to 4).
[D]Mean titer log10
[E]Mean sample/positive ratio
[F]Macroscopically scored from 0 to 4
[G]Mean thickness (μm)

Results

Transmissibility. Transmissibility results are presented in Table 3. At four weeks post introduction (PI) of the seeders, one commingled bird (direct contact) was culture positive for K5831B-19. At eight weeks PI the direct contacts had a low level of infection (2/15) by culture and serology. At sixteen weeks PI most of the direct contacts (12/14) were infected with K583113-19. The vaccine did not transmit to birds in an adjacent pen separated by wire mesh or to birds separated by an empty pen. These data are graphically presented in FIG. 1.

TABLE 3

(Transmissibility). Serological response and MG isolation from the choanal cleft of chickens post challenge with K5831B-19 strain by eye drop (seeders), direct contact, indirect contact between neighboring pens (adjacent) or with an empty pen separating.

| Weeks Post challenge | K5831B-19 Contact | SPA | HI | ELISA | MG isolation |
|---|---|---|---|---|---|
| 1 | Seeders | 5/5[A] (4.0)[B] | 3/5 (0.8)[C] | 0/5 (0.0)[D] | 5/5 |
| | Direct | 0/15 (0.0)[B] | 0/15 (0.0) | 0/15 (0.0) | 0/15 |
| | Adjacent | 1/5 (0.2) | 0/5 (0.0) | 0/5 (0.0) | 0/5 |
| | Empty pen | 0/5 (0.0) | 0/5 (0.0) | 0/5 (0.0) | 0/5 |
| 2 | Seeders | 5/5 (4.0) | 5/5 (1.5) | 0/5 (0.1) | 5/5 |
| | Direct | 0/15 (0.0) | 0/15 (0.0) | 0/15 (0.0) | 0/15 |
| | Adjacent | 0/5 (0.0) | 0/5 (0.0) | 0/5 (0.0) | 0/5 |
| | Empty pen | 0/5 (0.0) | 0/5 (0.0) | 0/5 (0.0) | 0/5 |
| 4 | Seeders | 5/5 (4.0) | 5/5 (1.8) | 5/5 (0.9) | 5/5 |
| | Direct | 0/15 (0.0) | 0/15 (0.0) | 0/15 (0.0) | 1/15 |
| | Adjacent | 0/5 (0.0) | 0/5 (0.0) | 0/5 (0.0) | 0/5 |
| | Empty pen | 0/5 (0.0) | 0/5 (0.0) | 0/5 (0.0) | 0/5 |
| 8 | Seeders | 5/5 (4.0) | 5/5 (1.9) | 5/5 (2.1) | 5/5 |
| | Direct | 2/15 (0.5) | 3/15 (0.3) | 0/15 (0.1) | 2/15 |
| | Adjacent | 0/5 (0.0) | 0/5 (0.0) | 0/5 (0.0) | 0/5 |
| | Empty pen | 0/5 (0.0) | 0/5 (0.0) | 0/5 (0.0) | 0/5 |
| 12 | Seeders | 5/5 (4.0) | 5/5 (1.7) | 5/5 (2.2) | 5/5 |
| | Direct | 1/15 (0.3) | 1/15 (0.1) | 1/15 (0.1) | 1/15 |
| | Adjacent | 0/5 (0.0) | 0/5 (0.0) | 0/5 (0.0) | 0/5 |
| | Empty pen | 0/5 (0.0) | 0/5 (0.0) | 0/5 (0.0) | 0/5 |
| 16 | Seeders | 5/5 (3.8) | 5/5 (1.8) | 5/5 (3.0) | 5/5 |
| | Direct | 11/14 (2.6) | 10/14 (1.2) | 6/14 (0.6) | 12/14 |
| | Adjacent | 0/5 (0.0) | 0/5 (0.0) | 0/5 (0.0) | 0/5 |
| | Empty pen | 0/5 (0.0) | 0/5 (0.0) | 0/5 (0.0) | 0/5 |
| 20 | Seeders | 4/4 (4.0) | 5/5 (1.8) | 4/4 (2.3) | 4/5 |
| | Direct | 13/14 (3.7) | 13/14 (1.7) | 13/14 (1.4) | 13/14 |
| | Adjacent | 0/20 (0.0) | 0/20 (0.0) | 0/20 (0.0) | 0/18 |
| | Empty pen | 0/20 (0.0) | 0/20 (0.0) | 0/20 (0.0) | 0/18 |

[A]No. of positive samples/No. of tested samples (SPA: ≥1, HI: ≥40, and ELISA: ≥0.6)
[B]Mean agglutination grade (from 0 to 4).
[C]Mean Titer Log10
[D]Geometric mean sample/positive ratio ± standard deviation

TABLE 4

Serological response and MG isolation from chickens post inoculation with K5831B-19[A].

| Weeks Post challenge | SPA | HI | ELISA | Air sac lesion score | Tracheal mucosal thickness | Tracheal Score | MG isolation Trachea | Air sacs |
|---|---|---|---|---|---|---|---|---|
| 1 | 5/5[B] (4.0)[C] | 4/5 (1.1)[Da] | 0/5 (0.01)[Ea] | 0/5 | 60.6 ± 8.0 | 0.0 | 5/5[a] | 4/5[a] |
| 2 | 5/5 (4.0) | 5/5 (1.5)[ab] | 0/5 (0.19)[a] | 0/5 | 58.4 ± 10.8 | 0.0 | 5/5[a] | 2/5[ab] |
| 4 | 5/5 (4.0) | 5/5 (1.8)[b] | 2/5 (0.39)[ab] | 0/5 | 69.7 ± 7.6 | 0.0 | 5/5[a] | 1/5[b] |
| 8 | 5/5 (4.0) | 5/5 (1.7)[b] | 5/5 (1.36)[bc] | 0/5 | 89.2 ± 9.6 | 0.0 | 5/5[a] | 0/5[b] |
| 12 | 5/5 (4.0) | 5/5 (1.8)[b] | 5/5 (2.17)[cd] | 0/5 | 192.2 ± 94.3 | 0.2 | 5/5[a] | 0/5[b] |
| 16 | 5/5 (4.0) | 5/5 (1.8)[b] | 5/5 (2.80)[d] | 0/5 | 116.6 ± 5.2 | 0.0 | 3/4[a] | 0/5[b] |
| 20 | 5/5 (4.0) | 5/5 (1.7)[ab] | 5/5 (2.58)[d] | 0/5 | 134.1 ± 30.4 | 0.0 | 3/5[a] | 0/5[b] |

Figure 2:
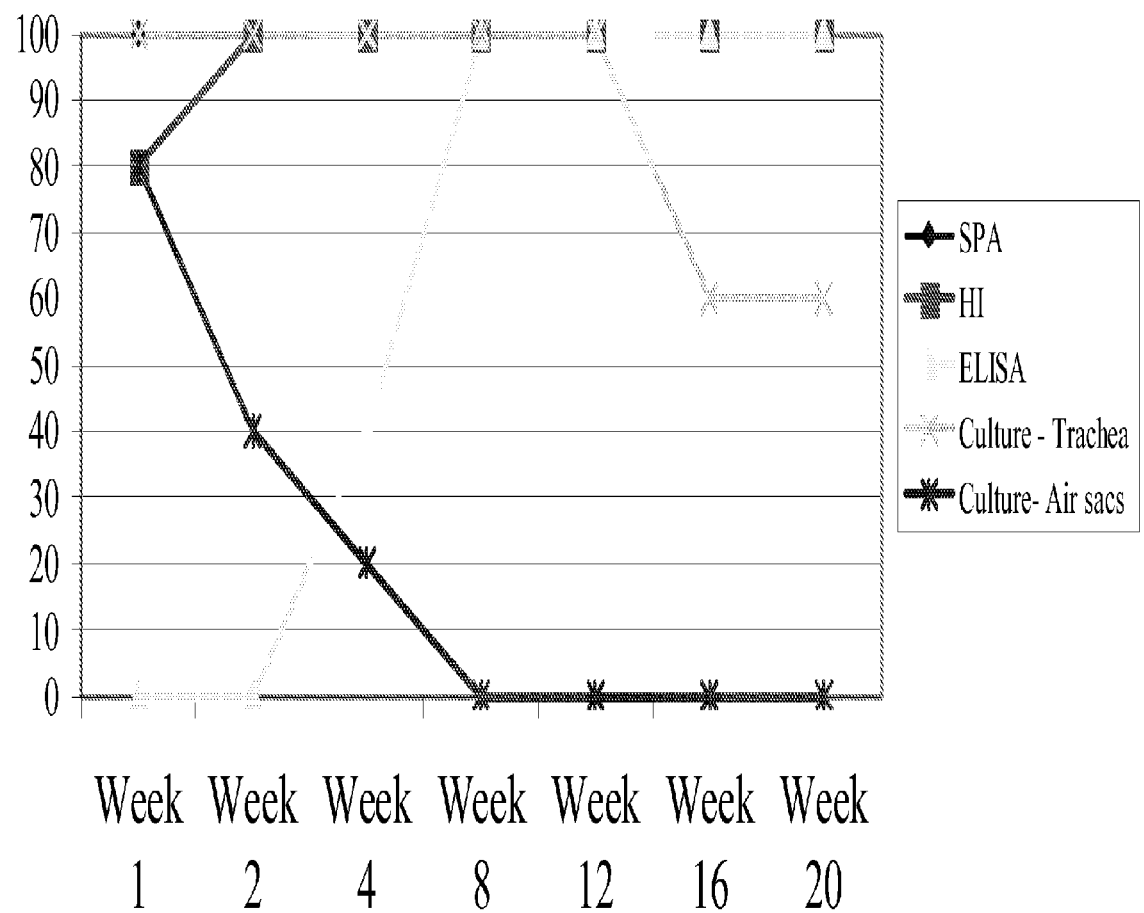
FIG. 2 is a graph depicting the summary of results of an excretion study. Results are shown as % positive.
Figure 3:
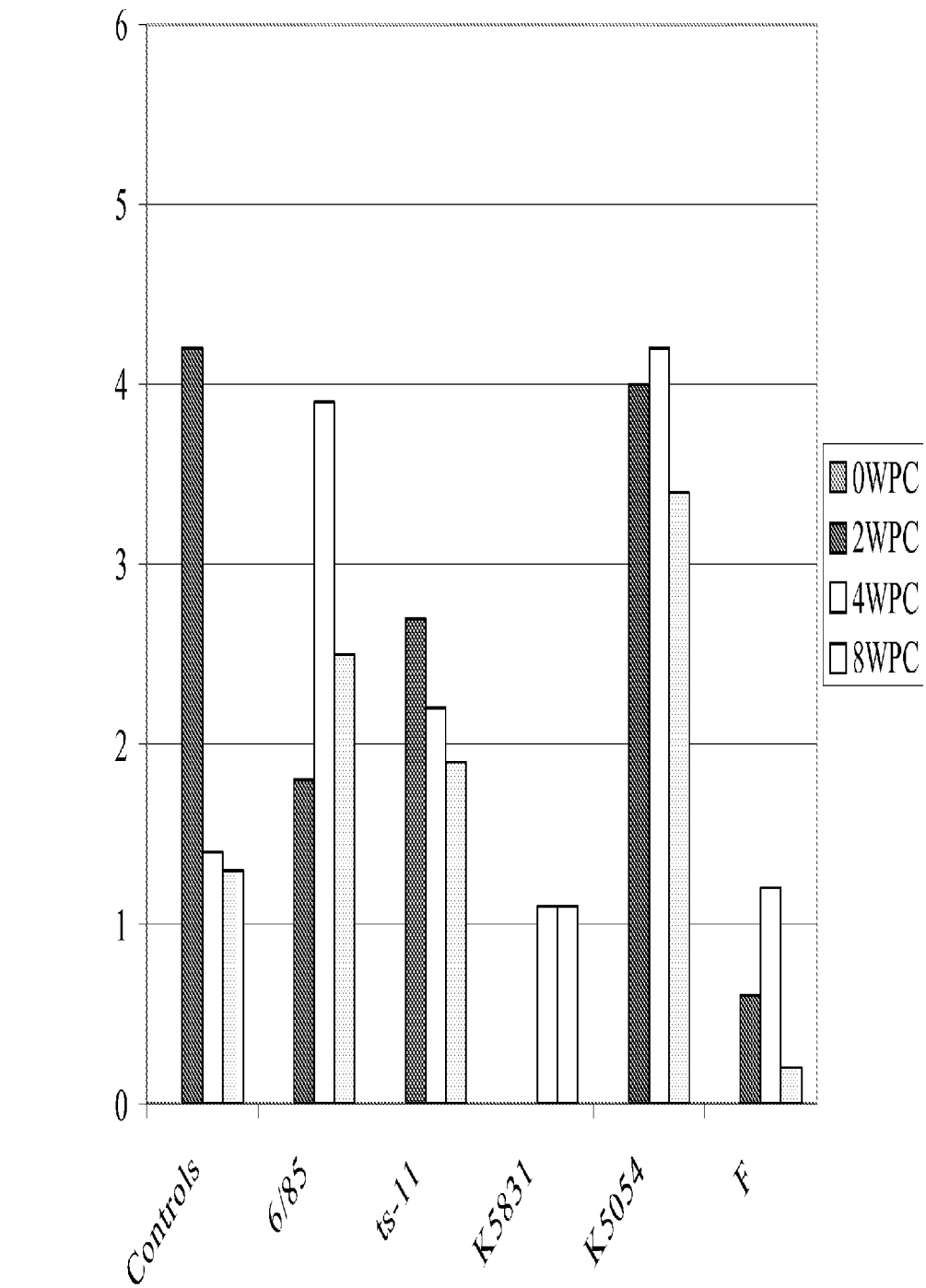
FIG. 3 is a graph depicting displacement study results, in copy numbers (Log 10) of R-strain in vaccinated chickens and non-vaccinated chickens (controls) at 0, 2, 4 and 8 weeks post introduction of R-strain seeders.
Figure 4:
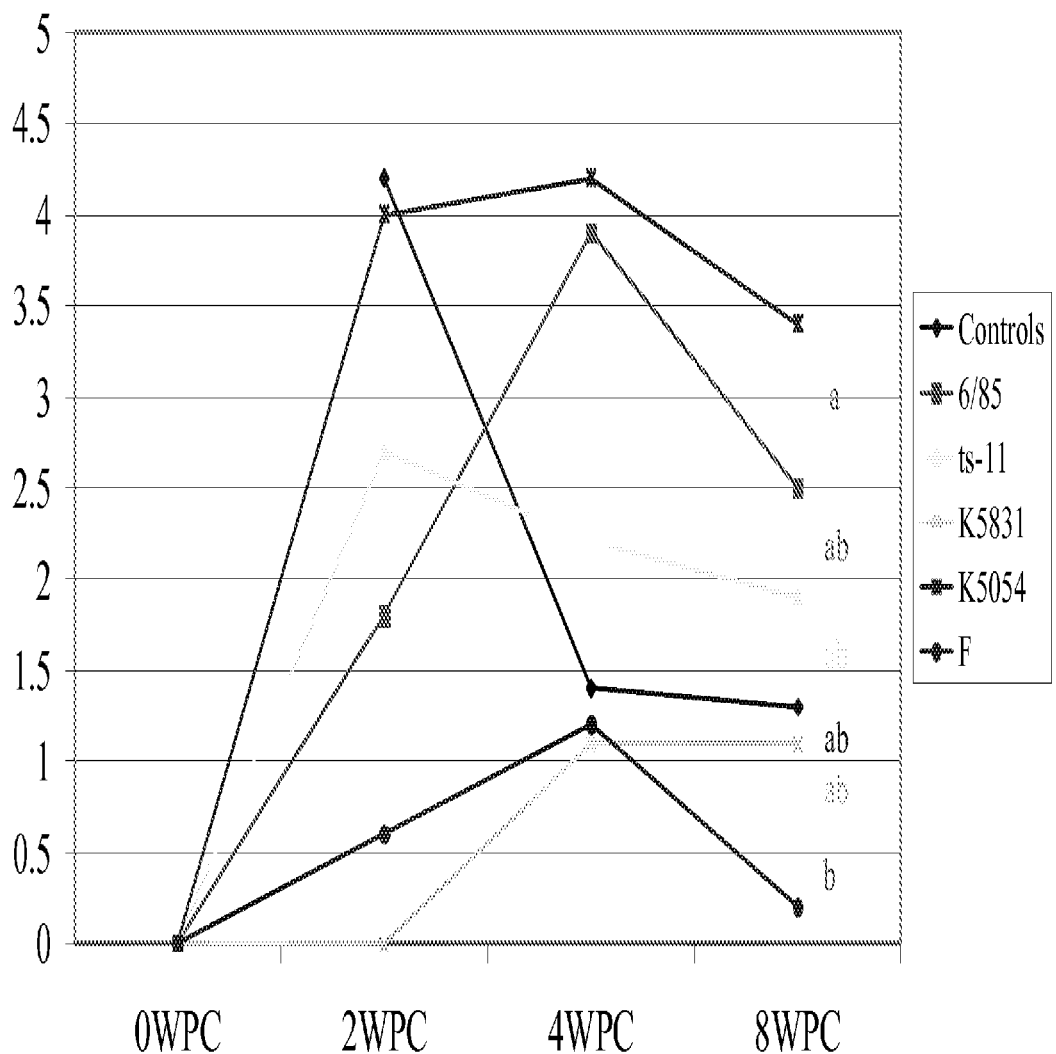
FIG. 4 is a graph depicting displacement study results, in copy numbers (Log 10) of R-strain in vaccinated chickens and non-vaccinated chickens (controls) at 0, 2, 4 and 8 weeks post introduction of R-strain seeders.
Figure 5:
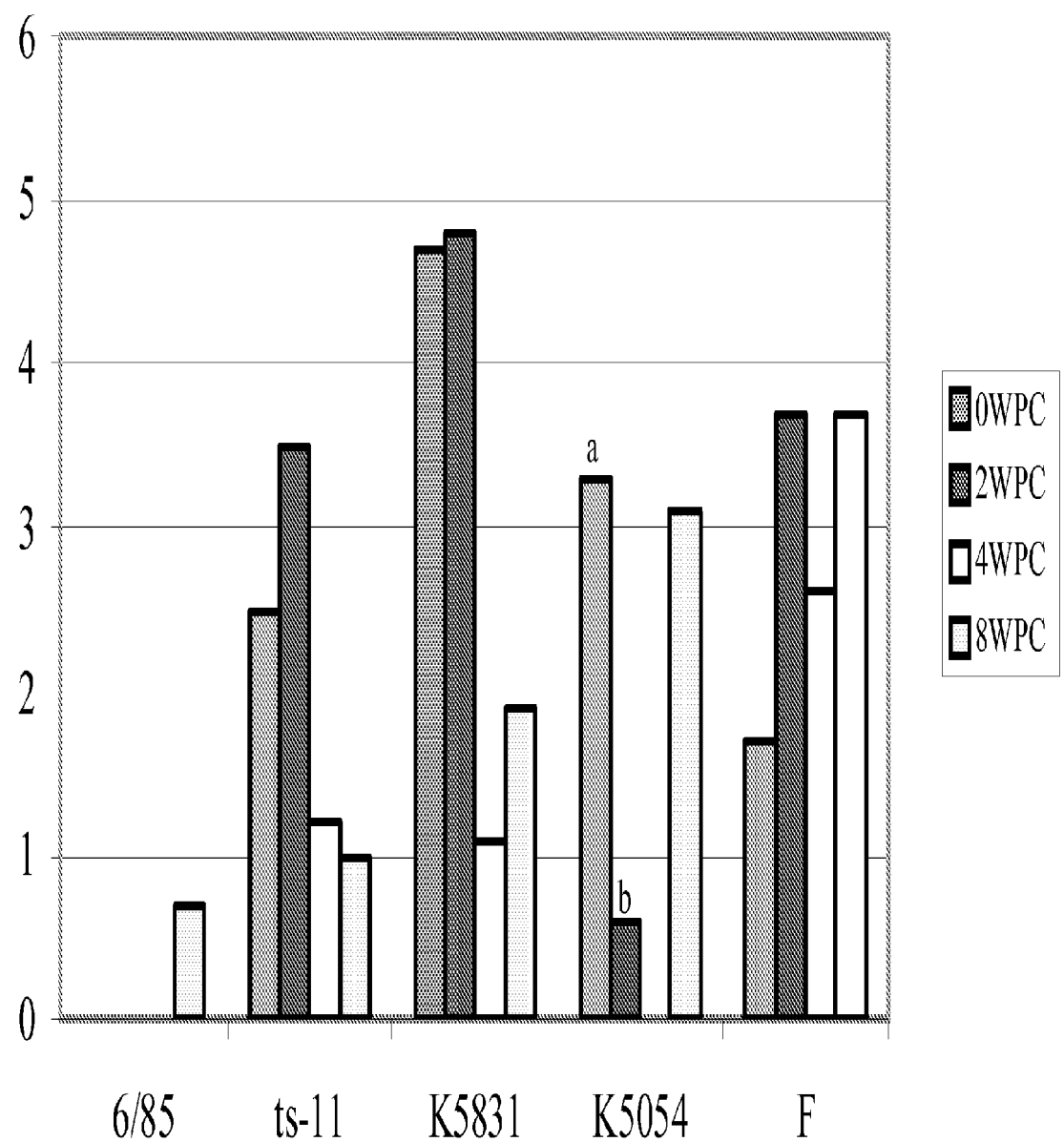
FIG. 5 is a graph depicting displacement study results, in copy numbers (Log 10) of vaccines from chickens at 0, 2, 4 and 8 weeks post introduction of R-strain seeders.
Figure 6:
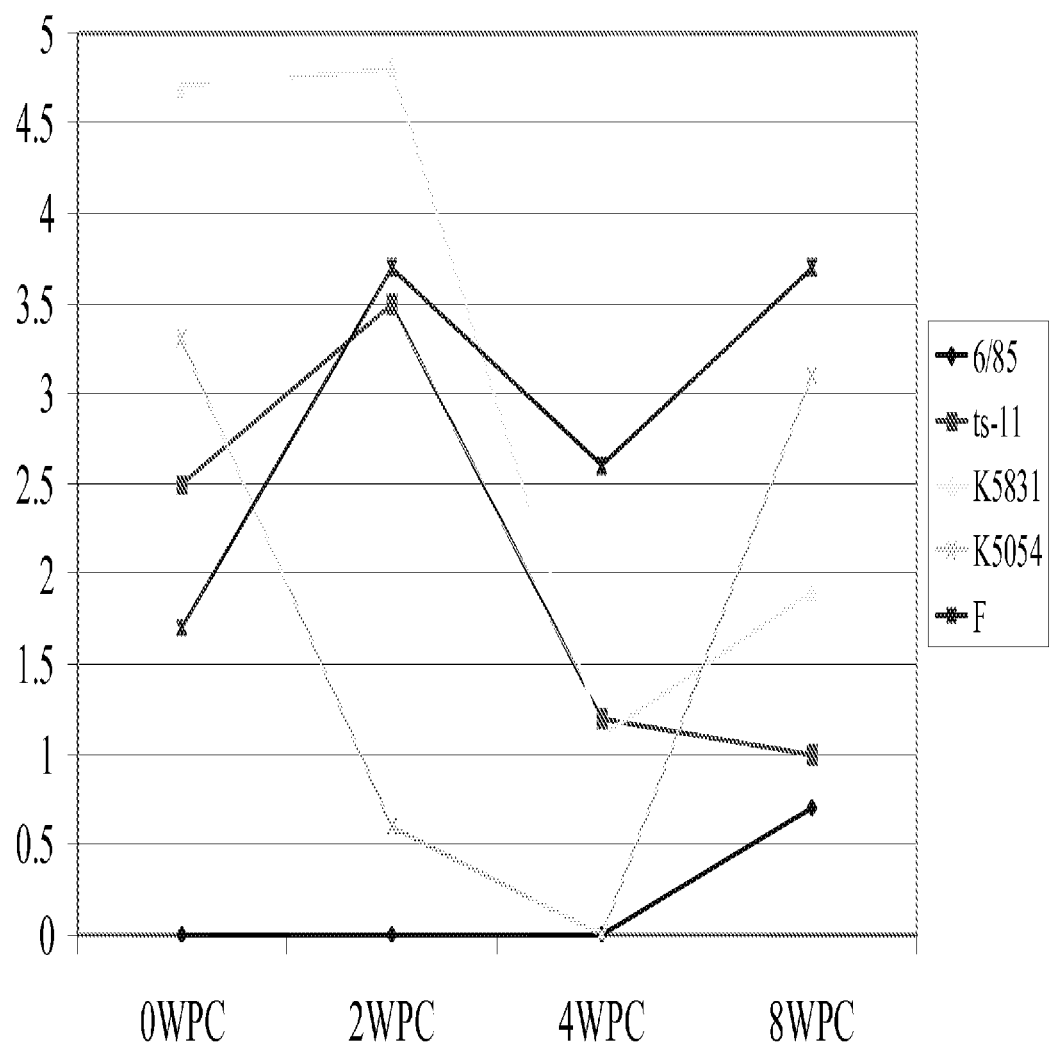
FIG. 6 is a graph depicting displacement study results, in copy numbers (Log 10) of vaccines from chickens at 0, 2, 4 and 8 weeks post introduction of R-strain seeders.

[A]Values within a column with a different lower case superscript are significantly different (P ≤ 0.05)
[B]No. of positive samples/No. of tested samples (SPA: ≥1, HI: ≥20, and ELISA: ≥0.5)
[C]Mean agglutination grade (from 0 to 4).
[D]Mean titer log10
[E]Mean sample/positive ratio Excretion. Excretion results are presented in Table 4. K5831B-19 was re-isolated from vaccinated birds up to 20 weeks post vaccination at which time the study was concluded. The incidence of re-isolation from the air sacs and trachea decreased over time. The vaccine was absent from the air sacs by eight weeks post vaccination and the incidence of recovery from the trachea decreased to 60% (3/5) at 20 weeks post vaccination. The birds continued to be seropositive at 20 weeks post vaccination. These data are graphically presented in FIG. 2.

In this study the majority of commingled chickens remained negative until 20 weeks of age after the onset of sexual maturity. It can be concluded that K5831B-19 has a relatively low rate of transmission. In this study, K5831B-19 persisted in the upper respiratory tract for the duration of the study (five months).

Example 3

Mycoplasma gallisepticum Strain K5831 Back Passage in Chickens

This example investigates the potential of Mycoplasma gallisepticum (MG) strain K5831 to cause disease in chickens following five back passages in chickens. The distribution of MG in the body of challenged chickens was also investigated.
Procedures Back Passage. Twenty-five SPF chickens were acquired at three weeks of age and housed in five isolation units. One group of five chickens was challenged with K5831B-19 via eye drop. At one week post challenge the tracheas of these birds were swabbed and these swabs were used to infect a second group of five chickens. K5831B-19 was back passaged in this manner five times. MG was re-isolated from infected chickens by inoculation of the tracheal swabs into modified Frey's broth after the swabs were used transfer the infection (K5866, K5969, K5872, and K5876). The final re-isolate of K5831B-19 (K5883-2) was used in the challenge study.

Challenge. Eighty commercial layer-type chickens were acquired from a source known to be free of MG and MS. These chickens were housed in four colony houses. At four weeks of age, eight chickens were screened to ensure that they were MG-free by serology and culture. At five weeks of age, three of the groups of chickens were challenged with log phase cultures of K5831B-19 ($2.59 \times 10^8$ CCU/ml), K5883-2 ($1.21 \times 10^7$ ccu/ml), and R strain ($1.15 \times 10^8$ ccu/ml) strain. One group was not challenged (negative controls). The birds were necropsied at ten days post challenge and evaluated by air sac lesion scoring, serology, and culture.

Body Distribution. In addition to the trachea and air sacs, six sites (kidney, liver, bursa, lungs, cecal tonsil, and spleen) from five birds challenged with K5831B-19 ($2.59 \times 10^8$ ccu/ml) above were cultured.

Random amplified polymorphic DNA (RAPD). RAPD analysis was used to fingerprint MG isolates. RAPD analysis and sequencing of four targeted genes (pvpA, mgc2, gapA and MGA_0319) were used to compare K2101, K5831B-19 and K5883-2. The procedure and primers used were as described by Fan et al. (Fan et al., 1995, Avian Dis; 39:729-735).

DNA sequence analysis. DNA sequences of isolates and reference strains were analyzed and compared as previously described (Ferguson et al., 2003, Avian Dis; 47(3):523-30). The sequences of the pvpA gene (Boguslaysky et al., 2000, Infect Immun; 68:3956-3964; and Liu et al., 2001, J Clin Microbiol; 39:1882-1888), a lipoprotein sequence (MGA_0319) (Nascimento et al., 1991, Avian Dis; 35:62-69), gapA (Goh et al., 1998, Microbiol; 44:2971-2978; and Keeler et al., 1996, Infect Immun; 64:1541-1547), and the mgc2 cytadhesin gene (Hnatow et al., 1998, Infect Immun; 66:3436-3442) were compared as previously described (Ferguson et al., 2005, Microbiol; 151:1883-1893). Sequence analysis was performed with MegAlign (DNASTAR, Lasergene, Inc. Madison, Wis.).

Quantitative strain differentiating real-time PCR. The larynxes of necropsied birds were collected in 4 ml sterile PBS tubes. One ml of a laryngeal wash (after vortexing samples for 30 seconds) was used for DNA extraction. The DNA extracts were subjected to Taqman real-time PCR with primers and probes capable of differentiating between the vaccines (K5831B-19, K5054, ts-11, 6/85, F-strain) and R-strain. The analysis was made quantitative by plotting the threshold cycle number (CT Value) on previously determined standard curves along with standardized controls for the reactions. (Raviv et. al., 2008, Vet Microbiol; 129(1-2):179-87).
Results Back Passage. RAPD and sequence analysis of K5831B-19 and K5883-2 showed no genetic changes resulting from back passage. Both demonstrate a K2101 RAPD pattern. RAPD results are shown in FIGS. 7 and 8.

Challenge. The challenge results are presented in Table 5. Challenge with the back passaged isolate (K5883-2) did not result in a significant increase in gross lesions (air sac scores) when compared to challenge with the original K5831B-19 and negative controls (P<0.05).

Body distribution. MG was recovered from the lungs (5/5) as well as the tracheas (20/20) of birds challenged with K5831B-19. MG was also re-isolated from 6 of 20 (30%) of the air sacs of these chickens. There were no isolations from the kidney, liver, bursa, cecal studies.

TABLE 5

K5831B-19 Backpassage. Serological response and lesion scores of chickens 10 days post challenge with K5831B-19, K883-2, or R strain[A].

| | | | | Air sac | MG isolation | |
| --- | --- | --- | --- | --- | --- | --- |
| Challenge | SPA | HI | ELISA | lesion score | Trachea | Air sacs |
| None | 0/20[B] (0.0)[Ca] | 0/20 (0.0)[Da] | 1/20 (0.1)[Ea] | 0/20 (0.0)[Fa] | 0/20[a] | 0/20[a] |
| K5831B-19 | 20/20 (2.0)[b] | 0/20 (0.0)[a] | 0/20 (0.0)[a] | 0/20 (0.0)[a] | 20/20[b] | 6/20[b] |

TABLE 5-continued

K5831B-19 Backpassage. Serological response and lesion scores of chickens
10 days post challenge with K5831B-19, K883-2, or R strain[A].

| Challenge | SPA | HI | ELISA | Air sac lesion score | MG isolation Trachea | MG isolation Air sacs |
|---|---|---|---|---|---|---|
| K5883-2 | 20/20 (2.0)[b] | 17/20 (1.2)[b] | 9/20 (0.6)[b] | 1/20 (0.1)[a] | 20/20[b] | 15/20[c] |
| R strain | 20/20 (2.2)[b] | 20/20 (1.9)[c] | 17/20 (1.1)[c] | 18/20 (2.0)[b] | 20/20[b] | 19/20[c] |

[A]Values within a column with a different lower case superscript are significantly different (P ≤ 0.05)
[B]No. of positive samples/No. of tested samples (SPA: ≥1, HI: ≥20, and ELISA: ≥0.5, Air sac score ≥1)
[C]Mean agglutination grade (from 0 to 4).
[D]Mean titer log10
[E]Mean sample/positive ratio
[F]Mean score Discussion K5831B-19, a naturally occurring MG strain of low virulence may have the advantage of increased stability over many in vivo passages when compared to laboratory attenuated vaccine strains. This example demonstrates that there is no increase in virulence of K5831B-19 when back passaged five times through chickens and gross lesions following challenge are assessed. From the body distribution analysis, this example also demonstrates that K5831B-19 remains primarily in the respiratory system of challenged birds.

Example 4

*Mycoplasma gallisepticum* Strain K5831 Vertical Transmission

This example investigate the potential of *Mycoplasma gallisepticum* (MG) strain K5831B-19 to transmit from infected chickens to embryos.

Procedures

Thirty female and nine male layer-type chickens were acquired from a source free of *Mycoplasma*. The birds were housed in three pens (ten females and three males per pen). At 25 weeks of age (approximately 80% production) five chickens were screened for *Mycoplasma* by culture and serology. At 25.3 weeks of age the chickens were challenged by aerosol with K5831B-19 ($6.2 \times 10^8$ ccu/ml). Eggs were collected daily from 24 weeks of age until the end of the study. The yolk sacs of 18-day-old incubated embryos were cultured for *Mycoplasma*. At 32 weeks of age the chickens were necropsied and evaluated.

Results

The chickens were negative for *Mycoplasma* by serology and culture at the pre-vaccination screening.

Embryo culture. *Mycoplasma* was not recovered from any of the embryos during the study.

Trachea and air sac culture. MG was recovered from 35/36 (97%) tracheal swabs but from only 4/36 (11%) air sac swabs at seven weeks post vaccination.

Serology. At seven weeks post vaccination all of the chickens had seroconverted to MG.

Tracheal and air sac lesions. No air sac lesions seen at necropsy. A few of the birds had very mild tracheal lesions consisting of lymphocytic infiltration, mucus gland hyperplasia, and cilia loss.

For the evaluation of lesions, the lesions in chickens necropsied during the study were evaluated grossly by air sac lesions scoring on a scale from 0 to 4 (Kleven et al., 1972, *Avian Dis;* 16:915-924). The tracheal lesions were evaluated microscopically by measuring the width of the tracheal mucosa. A section was collected from the upper third of the trachea (approximately one inch distal from the larynx) and fixed in 10% neutral formalin. The tracheal mucosa thickness was measured at four equidistant points on histological slides of cross sections of tracheas. Tracheal lesions were also scored from 0 to 3. With the statistical analysis, air sac lesion scores, tracheal scores and SPA scores were analyzed using the Kruskal-Wallis Rank Sums test. The mean tracheal mucosa thickness, HI titers log 10, ELISA S/P ratios, and copy numbers log 10 were analyzed using the Tukey-Kramer HSD test. JMP® Statistics Made Visual (SAS Institute Inc., SAS Campus Drive, Cary, N.C. 27513).

Discussion

With this example, no K5831B-19 was detected in embryonated eggs. The strain must become systemic to pass through the reproductive tract to the offspring. From earlier studies, K5831B-19 seems to remain primarily in the upper respiratory tract and although it can be recovered from this area for relatively long periods of time after vaccination (up to 20 weeks), recovery from the air sacs is more variable and diminishes over a few weeks. This example also demonstrates that, if K58318-19 is transmitted through eggs at all, it is at a very low rate that could not be detected under these experimental conditions.

Example 5

*Mycoplasma gallisepticum* Vaccine Displacement

This example investigates the potential of *Mycoplasma gallisepticum* (MG) vaccines K5831B-19, K5054, ts-11, 6/85, and F strain to displace virulent strains in infected chickens.

Procedures

One hundred and twenty-seven MG/MS free layer-type chickens were acquired at one day of age from a commercial source. At three weeks of age, ten chickens were screened for *Mycoplasma* by culture and serology. At eight weeks of age, groups of 20 chickens were vaccinated with K5831B-19, K5054, ts-11, 6/85, and F-strain. At 13.3 weeks of age a group 12 chickens (seeders) were inoculated with R strain via eye drop. At 14 weeks of age, five chickens from each of the vaccinated groups were necropsied and evaluated (Necropsy 1). At this time (six weeks post vaccination), two seeders were commingled with the remaining 15 chickens in each of the vaccinated groups and 15 naive chickens (challenged controls). The chickens were stressed by vaccination with Newcastle/Infectious Bronchitis at this time. Two weeks after the introduction of the seeders, five birds from each of the groups were removed, necropsied and evaluated (Necropsy 2). This procedure was repeated at four and eight weeks post challenge (Necropsy 3 and 4). At each necropsy, evaluation consisted of culture, serology, air sac lesions scoring, histopathology of tracheas, and quantitative PCR (Q-PCR) analysis.

Vaccination. The 6/85 (Mycovac-L® Intervet, Millsboro, Del.) and F-strain (F Vax-MG® Schering-Plough Animal Health Corporation, Summit, N.J.) vaccines were administered by coarse spray using a commercial paint sprayer (Preval Sprayer Division, Precision Valve Corporation, Yonkers, N.Y.). These lyophilized vaccines were reconstituted according to the manufacturers instructions with distilled water to a concentration of 1 dose/ml. K5831B-19 and K5054 were also administered by coarse spray as fresh actively growing cultures. The log phase cultures were diluted 1:10 with Frey's modified broth before application to more closely approximate the dose of the commercial vaccines. Approximately one milliliter (ml) of culture was administered per bird. The ts-11 vaccine (Menial Select, Gainesville, Ga.) was thawed administered by eye drop according to the manufacturers instructions. All of the groups were also vaccinated with Newcastle-Bronchitis (Poulvac® Aero, Fort Dodge Animal Health, Fort Dodge, Iowa) via coarse spray according to the manufacturers directions.

Challenge. R-strain is a virulent MG strain. It was administered by eye drop (100 μl/bird) to the seeders.

Results

Serology. From the serological results of the first necropsy (six weeks post vaccination) all of the vaccinated groups had seroconverted to MG with the exception of the group vaccinated with 6/85. The ts-11 group seroconverted less strongly than the groups vaccinated with K58318-19, K5054 and F-strain. The 6/85 and ts-11 groups both lagged behind the other groups in terms of seroconversion until four to eight weeks after the introduction of the seeders.

Air Sac Lesions. At two weeks after the introduction of the seeders some of the birds had mild air sac lesions, probably associated with the Newcastle-Bronchitis vaccination.

Tracheal Lesions. Analysis of tracheal reactions was complicated by the introduction of the NDV/IB vaccine virus. There was also some reaction in the groups before the introduction of seeders and vaccine virus that may have been associated with environmental differences between the houses.

PCR. The groups vaccinated with K5831B-19 and F-strain lower copy numbers log 10 of R strain through out the study when compared to the other vaccines and the non-vaccinated controls. These differences were not always significant. There was no 6/85 detected in the group vaccinated with 6/85 until the final necropsy at eight weeks after the introduction of the seeders. It should be noted that all of the seeders were infected with the respective vaccines.

Discussion

The results of this example are presented in Tables 6 and 7 and FIGS. 3-6. This example demonstrates that the K5831B-19 and F-strain vaccines resulted in the lowest copy numbers log 10 of R strain, indicating lower colonization with R strain. These vaccines may be very useful for preventing infection with virulent wild type strains and so displacing circulating endemic strains from poultry operations.

TABLE 6

Serological response, lesion scores, MG isolation and quantitative PCR from vaccinated chickens commingled with seeders infected with R-strain[A].

| Weeks Post Challenge | Vaccine | SPA | HI | ELISA | Air sac lesion score | Tracheal mucosal thickness |
|---|---|---|---|---|---|---|
| 0 | None | ND | ND | ND | ND | ND |
|  | 6/85 | 0/5[C] (0.0)[D] | 0/5 (0.0)[E] | 0/5 (0.19)[F] | ND | 107.5 ± 12.8[b] |
|  | ts-11 | 4/5 (2.6) | 3/5 (0.8) | 3/5 (0.88) | ND | 99.6 ± 15.7[b] |
|  | K5831 | 5/5 (3.6) | 5/5 (1.4) | 5/5 (2.01) | ND | 105.8 ± 51.7[b] |
|  | K5054 | 5/5 (3.8) | 5/5 (1.4) | 4/5 (0.63) | ND | 142.8 ± 54.9[ab] |
|  | F-strain | 5/5 (4.0) | 5/5 (1.9) | 5/5 (3.33) | ND | 198.0 ± 53.5[a] |
| 2 | None | 5/5 (3.4) | 5/5 (1.5) | 4/5 (0.86) | 3/5 (0.8) | 581.1 ± 264.0[a] |
|  | 6/85 | 0/5 (0.0) | 0/5 (0.0) | 0/5 (0.13) | 1/5 (0.2) | 149.8 ± 30.5[b] |
|  | ts-11 | 5/5 (2.4) | 1/5 (0.3) | 2/5 (0.55) | 1/5 (0.4) | 156.5 ± 17.6[b] |
|  | K5831 | 5/5 (4.0) | 5/5 (1.7) | 5/5 (3.00) | 1/5 (0.2) | 444.5 ± 120.7[ab] |
|  | K5054 | 5/5 (4.0) | 5/5 (1.7) | 5/5 (2.11) | 1/5 (0.2) | 439.5 ± 315.8[ab] |
|  | F-strain | 5/5 (4.0) | 5/5 (1.7) | 5/5 (2.42) | 1/5 (0.2) | 303.8 ± 96.5[ab] |
| 4 | None | 5/5 (3.6) | 5/5 (1.7) | 2/5 (0.40) | 0/5 (0.0) | 478.5 ± 247.0[a] |
|  | 6/85 | 3/5 (1.2) | 2/5 (0.6) | 2/5 (0.59) | 0/5 (0.0) | 148.6 ± 18.8[b] |
|  | ts-11 | 5/5 (4.0) | 5/5 (1.5) | 4/5 (1.22) | 0/5 (0.0) | 173.9 ± 43.6[b] |
|  | K5831 | 5/5 (4.0) | 5/5 (1.8) | 5/5 (2.50) | 0/5 (0.0) | 186.3 ± 33.1[b] |
|  | K5054 | 5/5 (4.0) | 4/5 (1.3) | 5/5 (1.65) | 0/5 (0.0) | 211.2 ± 79.3[b] |
|  | F-strain | 5/5 (4.0) | 5/5 (1.6) | 5/5 (1.66) | 0/5 (0.0) | 183.4 ± 32.8[b] |
| 8 | None | 5/5 (3.4) | 4/5 (1.3) | 4/5 (1.67) | 0/5 (0.0) | 190.5 ± 55.1[ab] |
|  | 6/85 | 5/5 (4.0) | 5/5 (1.8) | 5/5 (3.55) | 1/5 (0.2) | 313.1 ± 108.5[a] |
|  | ts-11 | 5/5 (3.6) | 5/5 (1.7) | 4/5 (2.62) | 0/5 (0.0) | 263.9 ± 71.3[ab] |
|  | K5831 | 5/5 (4.0) | 5/5 (1.6) | 5/5 (4.13) | 0/5 (0.0) | 173.6 ± 23.1[b] |
|  | K5054 | 5/5 (3.8) | 5/5 (1.7) | 5/5 (1.54) | 0/5 (0.0) | 208.3 ± 51.1[ab] |
|  | F-strain | 5/5 (4.0) | 5/5 (1.5) | 5/5 (2.03) | 0/5 (0.0) | 195.9 ± 24.0[ab] |

| Weeks Post Challenge | Tracheal Score | MG isolation (C. Cleft) | Q-PCR Vaccine[B] | Q-PCR R strain |
|---|---|---|---|---|
| 0 | ND | ND | N/A | ND |
|  | 0.0 ± 0.0[b] | 0/5 | 0/5 (0.0 ± 0.0)[G] | 0/5 (0.0 ± 0.0)[G] |
|  | 0.0 ± 0.0[b] | 4/5 | 5/5 (2.5 ± 1.7) | 0/5 (0.0 ± 0.0) |
|  | 0.4 ± 0.9[b] | 5/5 | 5/5 (4.7 ± 0.9) | 0/5 (0.0 ± 0.0) |

TABLE 6-continued

Serological response, lesion scores, MG isolation and quantitative PCR from vaccinated chickens commingled with seeders infected with R-strain[A].

|   |   | | | | |
|---|---|---|---|---|---|
|   | | $1.4 \pm 0.5^a$ | 5/5 | 4/5 (3.3 ± 2.3) | 0/5 (0.0 ± 0.0) |
|   | | $1.8 \pm 0.4^a$ | 5/5 | 3/5 (1.7 ± 1.7) | 0/5 (0.0 ± 0.0) |
| 2 | | $2.6 \pm 0.9^a$ | 5/5 | N/A | 5/5 (4.2 ± 0.8)[a] |
|   | | $0.6 \pm 0.5^c$ | 1/5 | 0/5 (0.0 ± 0.0) | 3/5 (1.8 ± 2.5)[ab] |
|   | | $1.0 \pm 0.0^{bc}$ | 5/5 | 3/5 (3.5 ± 3.2) | 4/5 (2.7 ± 2.7)[ab] |
|   | | $2.6 \pm 0.5^a$ | 5/5 | 5/5 (4.8 ± 0.7) | 0/5 (0.0 ± 0.0)[b] |
|   | | $2.0 \pm 1.0^{ab}$ | 3/4 | 2/5 (0.6 ± 0.8) | 5/5 (4.0 ± 2.3)[a] |
|   | | $2.0 \pm 0.7^{ab}$ | 5/5 | 5/5 (3.7 ± 0.8) | 1/5 (0.6 ± 1.4)[ab] |
| 4 | | $2.4 \pm 0.9^a$ | 5/5 | N/A | 4/5 (1.4 ± 1.4)[ab] |
|   | | $0.8 \pm 0.4^b$ | 5/5 | 0/5 (0.0 ± 0.0) | 5/5 (3.9 ± 1.4)[ab] |
|   | | $1.2 \pm 0.4^{ab}$ | 5/5 | 2/5 (1.2 ± 1.9) | 3/5 (2.2 ± 2.4)[ab] |
|   | | $1.2 \pm 0.8^{ab}$ | 5/5 | 2/5 (1.1 ± 1.6) | 3/5 (1.1 ± 1.4)[b] |
|   | | $1.6 \pm 0.5^{ab}$ | 5/5 | 0/5 (0.0 ± 0.0) | 5/5 (4.2 ± 1.0)[a] |
|   | | $1.2 \pm 0.4^{ab}$ | 5/5 | 5/5 (2.6 ± 1.0) | 4/5 (1.2 ± 0.8)[b] |
| 8 | | $1.6 \pm 0.9^a$ | 4/5 | N/A | 3/5 (1.3 ± 1.7)[ab] |
|   | | $2.0 \pm 0.7^a$ | 5/5 | 2/5 (0.7 ± 1.0) | 5/5 (2.5 ± 1.0)[ab] |
|   | | $1.8 \pm 0.5^a$ | 4/5 | 3/5 (1.0 ± 1.0) | 3/5 (1.9 ± 1.8)[ab] |
|   | | $0.8 \pm 0.5^a$ | 5/5 | 4/5 (1.9 ± 1.1) | 2/5 (1.1 ± 1.5)[ab] |
|   | | $1.4 \pm 0.5^a$ | 5/5 | 5/5 (3.1 ± 0.6) | 5/5 (3.4 ± 0.9)[a] |
|   | | $1.0 \pm 0.7^a$ | 5/5 | 5/5 (3.7 ± 0.5) | 1/5 (0.2 ± 1.5)[b] |

[A]Values within a column with a different lower case superscript are significantly different (P ≤ 0.05)
[B]Quantitative PCR specific for respective vaccines for each group
[C]No. of positive samples/No. of tested samples (SPA: ≥1, HI: ≥20, and ELISA: ≥0.5)
[D]Mean agglutination grade (from 0 to 4).
[E]Mean titer log10
[F]Mean sample/positive ratio
[G]Mean copy number log10 ± SD
ND = Not Done
N/A = Not Applicable

TABLE 7

Serological response, lesion scores, MG isolation and quantitative PCR from seeders challenged with R-strain and commingled with vaccinated chickens.

| Weeks Post Challenge | Vaccine | SPA | HI | ELISA | Air sac lesion score | Tracheal mucosal thickness |
|---|---|---|---|---|---|---|
| 8 | None | 2/2[B] (4.0)[C] | 2/2 (1.6)[D] | 2/2 (2.25)[E] | 0/2 (0.0) | 171.2 ± 39.6 |
|   | 6/85 | 2/2 (4.0) | 2/2 (1.8) | 2/2 (1.01) | 1/2 (0.5) | 180.5 ± 23.5 |
|   | ts-11 | 2/2 (4.0) | 2/2 (1.9) | 2/2 (2.68) | 0/2 (0.0) | 267.7 ± 2.9 |
|   | K5831 | 2/2 (4.0) | 2/2 (1.8) | 2/2 (4.27) | 0/2 (0.0) | 195.1 ± 35.2 |
|   | K5054 | 2/2 (4.0) | 2/2 (1.6) | 2/2 (3.06) | 0/2 (0.0) | 243.8 ± 51.4 |
|   | F-strain | 2/2 (4.0) | 2/2 (1.8) | 2/2 (3.77) | 0/2 (0.0) | 185.7 ± 48.4 |

| Weeks Post Challenge | Tracheal Score | MG isolation (C. Cleft) | Q-PCR Vaccine[A] | Q-PCR R strain |
|---|---|---|---|---|
| 8 | 0.5 ± 0.7 | 2/2 | N/A | 1/2 (1.2 ± 1.8)[F] |
|   | 1.0 ± 0.0 | 2/2 | 2/2 (3.3 ± 0.2)[F] | 2/2 (1.4 ± 0.4) |
|   | 2.0 ± 0.0 | 1/2 | 2/2 (3.3 ± 0.7) | 0/2 (0.0 ± 0.0) |
|   | 1.5 ± 0.7 | 2/2 | 2/2 (3.5 ± 0.1) | 1/2 (0.3 ± 0.4) |
|   | 0.5 ± 0.7 | 2/2 | 2/2 (3.7 ± 0.0) | 2/2 (4.2 ± 0.1) |
|   | 1.5 ± 0.7 | 1/1 | 2/2 (3.8 ± 0.1) | 1/2 (0.9 ± 1.2) |

[A]Quantitative PCR specific for respective vaccines for each group
[B]No. of positive samples/No. of tested samples (SPA: ≥1, HI: ≥20, and ELISA: ≥0.5)
[C]Mean agglutination grade (from 0 to 4).
[D]Mean titer log10
[E]Mean sample/positive ratio
[F]Mean copy number log10 ± SD
N/A = Not Applicable

Example 6

Pathogenicity of *Mycoplasma gallisepticum* Strain K5831 in Embryonated Eggs The pathogenicity of *Mycoplasma gallisepticum* (MG) strain K5831 in embryonated eggs was determined by evaluation of the embryonated egg lethal dose ($ELD_{50}$) and comparing to that of R strain.

Embryonated egg lethal dose ($ELD_{50}$). 0.2 mL of 100 to $10^8$ ccu/ml diluted samples (K5831B-19 and R strain) was inoculated into ten six-day-embryonated eggs via yolk sac route. Over twelve days of incubation, the embryos were examined and the $ELD_{50}$ was calculated. Results of this example are shown in Tables 8 and 9.

Example 7

Biochemical, Biological and Serological Properties of *Mycoplasma gallisepticum* Strain K5831

With this example, the biochemical, biological and serological properties of *Mycoplasma gallisepticum* (MG) strain K5831 were evaluated.

Procedures

The properties of K5831B-19 were examined by the following tests:

1. Glucose fermentation test
2. Arginine hydrolysis test
3. β-NAD requirement test
4. Tetrazolium reduction test
5. Film and spot production test
6. Hemadsorption test
7. Growth inhibition test (GIT)
8. Metabolism inhibition test (MIT)

TABLE 8

K5831B-19 strain $ELD_{50}$

| Dilution | Approx no. of organisms (CCU) | Results | # Dead (- trauma) | # Unaffected | Cumulative Dead | Cumulative Unaffected | Proportion (Dead/Total) | % Dead | Approx. No. of organisms |
|---|---|---|---|---|---|---|---|---|---|
| 0 | 10*7 | 9/9 | 9 | 0 | 34 | 0 | 1.00 | 100 | 1003.7E+07 |
| 1 | 10*6 | 7/10 | 7 | 3 | 25 | 3 | 0.89 | 89 | 893720000 |
| 2 | 10*5 | 7/10 | 7 | 3 | 18 | 6 | 0.75 | 75 | 75372000 |
| 3 | 10*4 | 4/10 | 4 | 6 | 11 | 12 | 0.4S | 48 | 4837200 |
| 4 | 10*3 | 3/9 | 3 | 6 | 7 | 18 | 0.28 | 28 | 283720 |
| 5 | 10*2 | 2/10 | 2 | 8 | 4 | 26 | 0.13 | 13 | 13372 |
| 6 | 10*1 | 2/10 | 2 | 8 | 2 | 34 | 0.06 | 6 | 637.2 |
| 7 | 10 | 0/9 | 0 | 9 | 0 | 43 | 0 | 0 | 03.72 |
| 8 | 0 | 0/10 | 0 | 10 | 0 | 53 | 0 | 0 | 00 |

PD 0.92
End point $3.72 \times 10^{4.9}$ (309416 organisms)

TABLE 9

R strain $ELD_{50}$

| Dilution | Approx no. of organisms (CCU) | Results | # Dead (- trauma) | # Unaffected | Cumulative Dead | Cumulative Unaffected | Proportion (Dead/Total) | % Dead | Approx. No. of organisms |
|---|---|---|---|---|---|---|---|---|---|
| 2 | 10*5 | 10/10 | 10 | 0 | 44 | 0 | 1.00 | 100 | 100230000 |
| 3 | 10*4 | 10/10 | 10 | 0 | 34 | 0 | 1.00 | 100 | 10023000 |
| 4 | 10*3 | 8/9 | 8 | 1 | 24 | 1 | 0.96 | 96 | 962300 |
| 5 | 10*2 | 8/10 | 8 | 2 | 16 | 3 | 0.84 | 84 | 84230 |
| 6 | 10*1 | 5/10 | 5 | 5 | 8 | 8 | 0.50 | 50 | 5023 |
| 7 | 10 | 2/10 | 2 | 8 | 3 | 16 | 0.16 | 16 | 162.3 |
| 8 | 0 | 1/9 | 1 | 8 | 1 | 24 | 0.04 | 4 | 40 |

PD 0
End point $2.3 \times 10^1$ (23 organisms)
End point $2.3 \times 10^{0.2}$ (3 organisms)

Each test was conducted according to common methods described in more details in Methods in Mycoplasmology, Vol. I. S. Razin, J. G. Tully, Eds. 1983. Briefly: for the glucose fermentation test, materials were test medium (modified Frey's broth (with glucose)), control medium (modified Frey's broth without glucose), and log phase broth cultures of test strains. Method: 1:1000 dilutions of test cultures were made in the control medium. 0.1 ml of the diluted cultures were transferred to tubes containing the test medium and control medium. The tubes were incubated at 37 C for 24 hours and observed for color change.

For the arginine hydrolysis test, materials were test medium (modified Frey's broth with arginine), control medium (modified Frey's broth (without arginine)), and log phase broth cultures of test strains. Method: 1:1000 dilutions of test cultures were made in the control medium. The diluted cultures were inoculated into tubes containing the test medium and control medium. The tubes were incubated at 37 C and observed for two weeks for color change.

For the β-NAD requirement test, materials included test medium (modified Frey's broth without β-NAD), control medium (modified Frey's broth (with β-NAD)) and log phase broth cultures of test strains. Method: 1:1000 dilutions of test cultures were made in the test medium. The diluted cultures were inoculated into tubes containing the test medium and control medium. The tubes were incubated at 37 C and observed for growth (color change).

For the tetrazolium reduction test, materials included test medium (Tetrazolium Broth) and log phase broth cultures of test strains. Method: 1:1000 dilutions of test cultures were made in the test medium. The diluted cultures were inoculated into tubes containing the test medium. The tubes were incubated at 37 C and observed for growth and color change (pink to reddish purple).

For the film and spot production test, materials included egg yolk emulsion agar plates and log phase broth cultures of test strains. Method: Test strains were inoculated onto agar plates and incubated at 37 C. The plates were observed daily for 2 weeks for film and spots.

For the hemadsorption test, material included washed 10% suspension of chicken erythrocytes in PBS and agar plates with colonies of test strains. Method: 0.5% RBC suspension in 2 ml PBS was prepared and pipetted onto agar plates. The plates were incubated at 37 C for 30 minutes. The excess RBC suspension was poured off and the plates washed with 5 ml PBS. The plates were examined for adsorption of RBC to colonies.

For the growth inhibition test (GIT), material included antisera (MG and MS), sterile absorbent filter paper disks (6 mm diameter), broth cultures of test organisms, and modified Frey's agar plates. Method: The disks were saturated with MG or MS antisera. Plates were inoculated with 0.1 ml of diluted test cultures and spread evenly. The inoculum was allowed to be absorbed at room temperature. The disks were placed on the inoculated agar surfaces at least two cm apart. The plates were incubated at 37 C and examined for evidence of inhibition zones.

For the metabolism inhibition test (MIT), materials included modified Frey's broth (with glucose and NAD), broth cultures of test organisms, antisera (MG and MS), and microtiter Plate. Method: 25 µl of broth media was added to all wells of the microtiter plate. 25 µl of heat-treated MG or MS antisera was added to the first wells (except the controls) and serially diluted (two-fold). 50 µl of the appropriate diluted cultures (103-104 CCU/ml) was added to all the appropriate wells except the controls. 125 µl of broth was added to all the wells except the controls (which received 175 µl of media). The microtiter plates were sealed and incubated at 37 C. The plates were first read after 72 hours of incubation.

The following strains were tested:
K5831B-19
*M. gallisepticum* PG31
*Mycoplasma synoviae* WVU1853
*M. iowae* (Serotype I) (Arginine hydrolysis test only)
*M. gallinarum* (Serotype B) K285 (Film and spot production test only)

Results

Table 10 presents the data from these studies.

TABLE 10

Properties of *Mycoplasma gallisepticum* strain K2101 (K5831B-19)

| | | K5831 B-19 | *M. gallisepticum* PG-31 | *M. synoviae* WVU 1853 | *M. iowae* (Sero. I) | *M. gallinarum* (Sero. B) K285 |
|---|---|---|---|---|---|---|
| Glucose fermentation | | + | + | + | ND | ND |
| Arginine hydrolysis | | − | − | − | + | ND |
| β-NAD requirement | | − | − | + | ND | ND |
| Tetrazolium reduction | | + | + | $W^A$ | ND | ND |
| Film and spot production | | − | − | + | ND | + |
| Hemadsorption | | + | + | + | ND | ND |
| Growth inhibition (GIT) | Anti-MG | $5.5^B$ | 7.5 | 0 | ND | ND |
| | Anti-MS | 0 | 0 | 4.5 | ND | ND |
| Metabolism inhibition (MIT) | Anti-MG | $5120^C$ | 10240 | <20 | ND | ND |
| | Anti-MS | <20 | <20 | ND | ND | ND |

Example 8

Characterization of *Mycoplasma gallisepticum* Strain K5831 by Gene-Targeted Sequencing

*Mycoplasma gallisepticum* strain K5831B-19 was characterized by gene-targeted sequencing (GTS) analysis of portions of the putative cytadhesinpvpA gene, the cytadhesin gapA gene, the cytadhesin mgc2 gene, and an uncharacterized hypothetical surface lipoprotein-encoding gene designated genome coding DNA sequence (CDS) MGA_0319, following procedures described in more detail in Ferguson et al. (Ferguson et al., 2005, *Microbiol;* 151:1883-1893), which is incorporated by reference herein.

Briefly, nucleic acid was extracted from 150 to 250 μl of a culture grown in modified Frey's medium or frozen Frey's medium stock cultures stored with 5% (v/v) glycerol.

Genomic DNA was extracted using the QIAamp DNA Mini Kit (QIAGEN), following the manufacturer's recommendations. Forward and reverse sequences for the targeted genes were as follows. For the gapA the forward primer was gapA 3F, having a sequence of TTCTAGCGCTTTAGC-CCTAAACCC (SEQ ID NO:4), and the reverse primer was gapA 4R, having a sequence of CTTGTGGAACAG-CAACGTATTCGC (SEQ ID NO:5). For the MGA_0319 gene the forward primer was 1p 1F, having the sequence of CCAGGCATTTAAAAATCCCAAAGACC (SEQ ID NO:6), and the reverse primer was 1p 1R, having a sequence of GGATCCCATCTCGACCACGAGAAAA (SEQ ID NO:7). For the mgc2 gene the forward primer was mgc2 1F, having a sequence of GCTTTGTGTTCTCGGGTGCTA (SEQ ID NO:8), and the reverse primer was mgc2 1R, having a sequence of CGGTGGAAAACCAGCTCTTG (SEQ ID NO:9). For the pvpA gene the forward primer was pvpA 3F, having a sequence of GCCAMTCCAACTCAA-CAAGCTGA (SEQ ID NO:10), and the reverse primer was pvpA 4R, having a sequence of GGACGTSGTCCTGGCTG-GTTAGC (SEQ ID NO:11).

All amplifications were performed in a PTC-200 DNA Engine MJ thermocycler (MJ Research) at 94° C. for 3 minutes, and 40 cycles of 94° C. for 20 seconds, 55 to 60° C. for 40 seconds 72° C. for 60 seconds, and 72° C. for 5 minutes. The optimal annealing temperature utilized to amplify the MGA_0319 and pvpA genes was 55° C., to amplify the mgc2 gene an annealing temperature of 58° C. was utilized, and 60° C. was utilized to amplify the gapA gene. PCR products were detected with UV light in a 2% agarose gel containing μg ethidium bromide/ml. The amplified gene fragment was sequenced using an Applied Biosystems Prism 377 automated sequencer (PE Applied Biosystems). Each amplification product was sequenced in both directions with the forward and reverse amplification primers. Complete overlapping of complementary sequences was performed using the SEQMAN program (in LASERGENE; DNAS-TAR).

GTS analysis of the MGA_0319 gene in Mycoplasma gallisepticum strain K5831B-19 yielded the following sequence: ATGAGAGCTT ATAACCAATT CATTACTAGA GGGTTGGACA GTTATGTAAA TAGTACAACT AAAGGGATTA ATATTCCCAA CAACTTATCA TCA-GATTCTG GTGGTAAGTT GTTAATGACT GCTTCT-GATA TGTTCGATAG TTTTGACGTA TCATTTAGTG CAGCTTATGT TCAACAATAT TTAAAACAAA CTAATAATAC TAACCGTGAT ACTGTTGGTG TAGT-TCAATC AGATATTGAT GAGATCAATC TGATGAATAA TTTCATTAGA GCTAAGGCAA ATGGTAACAC AAC-CAACACC TACTCACAAC AGATTACTAA TAAT-TCATTA TTAAAAACTG GTGAAGCGAA TCGAAC-TACT GATCCATATT ACAATGCTTA TGCAGATTTA GCAGCTGGAA CTAAAGATAT CCACGAAATC TTTGAATGAA ATGGGATGAA GACAGTTGAT TCTTC-GAAAT CAGATAATTC ATCAACAAAC GTAATGAGTA AAAAT (SEQ ID NO:12).

GTS analysis of the pvpA gene in Mycoplasma gallisepticum strain K5831B-19 yielded the following sequence: GGTAGtCCTA AGTTATTAGG TCCAAACCAA GCTG-GTCATC CACAACACGG ACCACGTCCG ATGAAT-GCTC ATCCAGGTCA ACCACGCCT CAACAAGCTG GCCCACGTCC AATGGGAGCT GGTGGATCTA ACCAACCAAG ACCAATGCCA AATGGTCTAC AAAACCCACA AGGTCCACGA CCAATGAACC CTCAAGGCGA TCCTCGTCCT CAACCAGCTG GTGT-CAGACC TAACAGCCCA CAAAATTCTC AAC-CACGCCC AATGCCAAAT AAACCACAAG GTCCAC-GACC AATGGGTGCT CCAAATCCTC AACCAGGCCC TCAACAAGCT GGCCCACGTC CAATGGGAGT TGGTGGATCT AACCAACCAA GACCAATGCC AAATCGTCCA CAAAACCCAC AAGGTCCACG ACCAATGAAC CCTCAAGGCG ATCCTCGTCC TCAACCAGCT GgtGTc (SEQ ID NO:13).

GTS analysis of the mgc2 gene in Mycoplasma gallisepticum strain K5831B-19 yielded the following sequence: TTT-TATCCAG TAGTGGGTGC AGGTGCTGGG TTGAT-TGTTG TTTCTTTACT CTTGGGTTTA GGGATTGGGA TTCCGATCGC TAAGAAAAAA GAAAGAATGA TGATCCAAGA ACGTGAAGAA CACCAAAAGA TGGT-TGAATC CCTTGGTATA ATCGAAGAAC AAAATAAAAC AGAAGCGATT GAGCCAACTG CAG-CAGTGCC AACTGAAGAA GTTAATACTC AAGAAC-CAAC TCAACCAGCT GGTGTTAATG TAGCTAATAA CCCTCAGATG GGGATCAATC AACCAGGATT TAAT-CAACCT CAGATTAATC CGCAATTTGG TCCTAATCCC CAACAAAGAA TTAACCCACA GGGCTTTGGT GGC-CCAATGC CACCTAACCA AATGGGAATG CGAC-CAGGGT TTAACCAAAT GCCCCCACAA ATGGGAG-GAA TGCCACCTAA CCAAATGGGA ATGCGACCAG GGTTTAACCA AATGCCCCCA CAAATGGGAG GAAT-GCCACC AAGACCAAAC TTCCCTAACC AAATGC-CTAA TATGAATCAA CCAAGACCAG GTTTCAGACC ACAACCTGGT GGTGGGGTGC CGATGGGAAA TAAAGCTGTA GGTGGGTTTA ATCAC (SEQ ID NO:14).

GTS analysis of the gapA gene in Mycoplasma gallisepticum strain K5831B-19 yielded the following sequence: CCTAACCGAA TTACTAACCC ATTAATGAAT AGAGATAACG TAATCGGTCA AGGTGCGTTC ATTAG-TAGAA ATGATATTCC ATCATCATTC TTTGAAAACA AAATTAATGA TATTGTAACT ACAGAAGCTG ATGG-TAAAGA AGTATTAGAT AGTAAATACA TTAATTCAAT CTATAGATAT ACTCCACCTC AAAACAATCC TGATATTAGA TTAAGATTAT TAGTAATTGA TCGT-TCTAGA GCAACTAATG ACTTCATTAA GTTATTACCT CAAGTATTAG TTGATGGCGA ATACGTTGCT GTTC-CACAA (SEQ ID NO:15).

GTS analysis characterizes K5831B-19 as gapA sequence type Va, MGA_0319 sequence type Va, mgc2 sequence type IVa, pvpA sequence type IIIa, mgc2/pvpA sequence type IIIa, and gapA/MGA_0319/mgc2/pvpA sequence type VIIa, as described in Ferguson et al.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

| Sequence Listing Free Text | |
|---|---|
| SEQ ID NO: 1-11 and 16-18 | Synthetic oligonucleotide primers. |
| SEQ ID NO: 12 | Partial nucleotide sequence of the MGA_0319 gene in *Mycoplasma gallisepticum* strain K5831B-19 obtained by gene-targeted sequencing. |
| SEQ ID NO: 13 | Partial nucleotide sequence of the pvpA gene in *Mycoplasma gallisepticum* strain K5831B-19 obtained by gene-targeted sequencing. |

| Sequence Listing Free Text | |
|---|---|
| SEQ ID NO: 14 | Partial nucleotide sequence of the mgc2 gene in *Mycoplasma gallisepticum* strain K5831B-19 obtained by gene-targeted sequencing. |
| SEQ ID NO: 15 | Partial nucleotide sequence of the gapA gene in *Mycoplasma gallisepticum* strain K5831B obtained by gene-targeted sequencing. |

What is claimed is:

1. An isolated *Mycoplasma gallisepticum* strain, wherein the isolated *Mycoplasma gallisepticum* strain is the K5831 *Mycoplasma gallisepticum* strain deposited at the ATCC under Patent Designation PTA-9495.

2. The isolated *Mycoplasma gallisepticum* of claim 1, wherein the isolated *Mycoplasma gallisepticum* is lyophilized.

3. A composition comprising the isolated *Mycoplasma gallisepticum* of claim 1.

4. The composition of claim 3 further comprising water.

5. The composition of claim 3 further comprising a pharmaceutically acceptable carrier.

6. The composition of claim 3, wherein the composition is formulated for mucosal administration.

7. The composition of claim 3, wherein the composition is formulated for intranasal, intraocular, or oral administration.

8. The composition of claim 3, wherein the composition is formulated for spraying or aerolizing.

9. A vaccine comprising the isolated *Mycoplasma gallisepticum* of claim 1.

10. The vaccine of claim 9, wherein the vaccine reduces the susceptibility of a birds of the order Galliformes to disease induced by *Mycoplasma gallisepticum*.

11. A method for reducing susceptibility of a bird of the order Galliformes against disease induced by *Mycoplasma gallisepticum*, the method comprising administering to the bird the K5831 *Mycoplasma gallisepticum* strain of claim 1.

12. The method of claim 11, wherein the K5831 *Mycoplasma gallisepticum* strain persists in the respiratory epithelium of the bird.

13. The method of claim 11, wherein the K5831 *Mycoplasma gallisepticum* strain excludes other *Mycoplasma gallisepticum* strains from the respiratory epithelium.

14. The method of claim 11, wherein the K5831 *Mycoplasma gallisepticum* strain is administered to the respiratory mucosa.

15. The method of claim 11, wherein the K5831 *Mycoplasma gallisepticum* strain is administered by eye drops, by aerosol, or by drinking water.

16. The method of claim 11, wherein the K5831 *Mycoplasma gallisepticum* strain is administered nasally.

17. The method of claim 11, further comprising administering at least one additional booster formulation to the bird.

18. The method of claim 11, wherein the bird is a chicken or turkey.

19. A method for protecting a bird of the order Galliformes against disease induced by *Mycoplasma gallisepticum*, the method comprising administering to the bird the K5831 *Mycoplasma gallisepticum* strain deposited at the ATCC under Patent Deposit Designation PTA-9495 of claim 1.

20. A kit comprising the isolated *Mycoplasma gallisepticum* of claim 1 and printed instructions, wherein the contents of the kit are contained within packaging material.

21. A vaccine for birds of the order Galliformes comprising an amount of the K5831 *Mycoplasma gallisepticum* strain, deposited at the ATCC under Patent Deposit Designation PTA-9495, sufficient to protect the birds of the order Gallifoinies from disease induced by *Mycoplasma gallisepticum*, and a pharmaceutically acceptable carrier.

22. The vaccine of claim 21, wherein the protective amount is that amount required for the K8531 *Mycoplasma gallisepticum* strain to colonize the upper respiratory tract of the bird.

23. The vaccine of claim 21, wherein the protective amount is between about 50 and about $5 \times 10^7$ color-changing units (ccu)/bird.

* * * * *